United States Patent
Isono et al.

[11] Patent Number: 5,871,477
[45] Date of Patent: Feb. 16, 1999

[54] MEDICAL CONTAINER WITH ELECTROLYTE SOLUTION STORED THEREIN

[75] Inventors: Keinosuke Isono, Kawaguchi; Hiroyuki Shichi; Hiroshi Motobayashi, both of Tokyo, all of Japan

[73] Assignee: Material Engineering Technology Laboratory, Incorporated, Tokyo, Japan

[21] Appl. No.: 757,227

[22] Filed: Nov. 27, 1996

[30] Foreign Application Priority Data

Nov. 28, 1995 [JP] Japan .................................. 7-334053

[51] Int. Cl.⁶ .................................................. A61B 19/00
[52] U.S. Cl. .......................... 604/410; 604/408; 604/416; 206/219; 424/665
[58] Field of Search ..................... 604/403, 408, 604/410, 416; 206/219, 221; 383/38, 41, 904, 906; 424/665, 679, 680

[56] References Cited

U.S. PATENT DOCUMENTS 4,630,727  12/1986  Feriani et al. .

FOREIGN PATENT DOCUMENTS

| 0 132 632 A2 | 2/1985 | European Pat. Off. . |
| 0 161 471 A2 | 11/1985 | European Pat. Off. . |
| 0 556 547 A2 | 8/1993 | European Pat. Off. . |
| 3238649 | 4/1984 | Germany . |
| WO 87/03809 | 7/1987 | WIPO . |

*Primary Examiner*—Mark O. Polutta
*Assistant Examiner*—David J. Cho
*Attorney, Agent, or Firm*—Knobbe, Martens, Olson & Bear, LLP

[57] ABSTRACT

A medical container with an electrolyte solution stored therein is disclosed. It is formed of a resinmade container main body, a base solution compartment, at least one isolated compartment or connected compartment, and an openable portion. The base solution compartment is arranged in the container main body and is filled with the electrolyte solution in a state steamsterilized together with the container main body. The isolated compartment or connected compartment is arranged in the container main body, is isolated from the base solution compartment by an isolation wall interposed therebetween, and is filled with a bicarbonate. The openable portion permits aseptic communication between the base solution compartment and the isolated compartment or connected compartment by an operation from an outside of the container main body at the time of use. The openable portion is formed at at least a part of the isolation wall. This medical container makes it possible to store an electrolyte solution, dialysate or the like at a pH value close to that of the body fluid without inducing kidney problems, diarrhea, vomiting or the like due to acidosis or the like upon use.

17 Claims, 12 Drawing Sheets

MEDICAL CONTAINER WITH ELECTROLYTE SOLUTION STORED THEREIN

BACKGROUND OF THE INVENTION (a) Field of the Invention

This invention relates to a medical container with an electrolyte stored therein, and more specifically to a medical container which stores therein a body fluid replenisher to be administered through a peripheral vein or a central vein, such as an infusion solution, a dialysate for a circulatory system, such as an artificial kidney dialysate, or an electrolyte solution as a preserving solution for an organ or the like.

(b) Description of the Prior Art

Despite the inclusion of bicarbonate ions ($HCO_3^-$) at a certain specific concentration in the blood or tissue cells of the human body, either absolutely or practically no bicarbonate salt, carbonate salt or the like (hereinafter simply referred to as "bicarbonate" for the sake of brevity) is contained in an infusion solution for use in the treatment or the like of the human body, a dialysate or an organ (tissue) preserving solution, although certain particular electrolytes are contained therein.

For example, the concentration of bicarbonate ions in the plasma of the human body is generally around 24 mEq/l or so. When directly administering a bicarbonate into the body by infusion or when indirectly administering it by a blood dialysis or peritoneal dialysis, it is desired to add the bicarbonate in an amount such that the concentration of bicarbonate ions in the solution conforms with that of bicarbonate ions in the plasma. It is however to be noted that an infusion solution or the like is filled in a plastic-made medical container and is supplied to a hospital generally in a state completely sterilized by autoclave sterilization or the like. Bicarbonate ions are therefore caused to decompose substantially into carbon dioxide gas upon autoclave sterilization if a bicarbonate is added beforehand in the electrolyte in the container. Further, a bicarbonate, when filled as a diluted solution in a conventional plastic-made medical container, decomposes into carbon dioxide gas and is hence lost, even when the medical container is not subjected to autoclave sterilization.

Accordingly, no bicarbonate is used in infusion solutions, dialysates and the like and instead, a substance which can be yield bicarbonate ions in vivo is added. To maintain the concentration of bicarbonate ions constant in plasma or the like, an acetate, a lactate or the like is added as a substitute for a bicarbonate.

For example, a typical electrolyte-replenishing infusion solution contains $Na^+$ at 20 to 50 mEq/l, $K^+$ at about 20 mEq/l or so, $Cl^+$ at 20 to 50 mEq/l, and $CH_3 CH(OH)COO^+$ or $CH_3 COO^+$ at 30 mEq/l. In addition, glucose, fructose, xylitol, sorbitol or the like is contained at 1 to 10 wt.%.

The acetate or lactate serves to yield bicarbonate ions in vivo, thereby replenishing same. It also maintain the infusion solution acidic so that stability is retained in a container. Accordingly, an acetate or lactate is widely used in infusion solutions these days.

Further, an infusion solution has conventionally been used in a closed system, namely, by filling it in a plastic-made container of variable volume which does not require a bottle plug piercing needle or the like. Such a container is generally subjected to autoclave sterilization after it is filled with the infusion solution. The infusion solution may however undergoes discoloration during the autoclave sterilization if it contains a saccharide and has a high pH value. To cope with this potential problem, an electrolyte-replenishing infusion solution is prepared with its pH value lowered as much as permissible.

On the other hand, a peritoneal dialysate has, for example, the following composition and properties.

Electrolyte concentrations (mEq/l):

| | |
|---|---|
| $Na^+$ | 130 to 150 |
| $K^+$ | as needed |
| $Ca^{2+}$ | 1 to 6 |
| $Mg^{2+}$ | 0 to 3 |
| $Cl^-$ | 90 to 135 |
| $CH_3CH(OH)COO^-$ | 30 to 45 |
| Glucose (g/dl) | 1 to 8 |
| Osmotic pressure (mOsm/l) | 300–680 |
| pH | about 5.5 |

An acetate or lactate yields bicarbonate ions in vivo, and serves to replenish bicarbonate ions which are consumed during dialysis.

As organ-preserving solutions, Eurocollin's solution, Wisconsin's solution and the like have been proposed. The followings can be mentioned as illustrative components for the preparation of Eurocollin's solution:

| | |
|---|---|
| $K_2HPO_4$ | 7.40 g/l |
| $NaHCO_3$ | 0.84 g/l |
| $KH_2PO_4$ | 2.04 g/l |
| KCl | 1.12 g/l |
| $MgSO_4$ | 0.48 g/l |
| Heparin | 5,000 units/l |
| Osmotic pressure | 326 mOsm/kg |

It has also been proposed to have organ-preserving solutions added beforehand with antibiotics, physiologically-active proteins (insulin, antiplatelet factors, antidiuretic hormones, and the like), saccharides (glucose, mannitol, and the like), vitamins (vitamin C, vitamin E, and the like), organic acids (lactic acid, citric acid, and the like), nucleic acid bases (adenosine triphosphate, and the like), antihypertensives (calcium antagonists, β-adrenocaptive antagonists, angiotensin converting enzyme inhibitors, and the like), anticoagulants (heparin, and the like). Further, addition of drugs such as the phosphoric diester compounds disclosed in Japanese Patent Laid-Open No. 215801/1995 has also been proposed.

However, when an acetate or an organic acid such as citric acid are used in large amounts in such an electrolyte solution as practiced to date, the tendency of acidosis is observed in the body of a patient who cannot promptly decompose the acetate or the like, for example, in the body of a patient suffering from a liver problem. When the pH value of an infusion solution or the like is controlled as low as possible, a patient administered with the infusion solution is over-dosed with the acid or acids and may develop a kidney problem, diarrhea, vomiting or the like. Such symptoms are often observed especially when the pH value is 5.0 or lower.

With a view to overcoming such problems of an electrolyte solution and also making it as close as possible in composition to a body fluid or a tissue cell fluid, it may be contemplated to add a bicarbonate. As described above, however, resulting bicarbonate ions are decomposed upon autoclave sterilization or even during storage, tend to be lost gradually as carbon dioxide gas.

With the foregoing in view, it was then proposed in Japanese Patent Laid-Open No. 105905/1994 to fill a bicarbonate solution in a compartment and then to enclose the compartment with a covering material having gas barrier property so that bicarbonate ions can be prevented from being lost as carbon dioxide gas. However, a bicarbonate in the form of an aqueous solution is mostly decomposed during autoclave sterilization, thereby failing to fully overcome the above-described problems.

SUMMARY OF THE INVENTION

An object of the present invention is therefore to provide a medical container with an electrolyte solution, a dialysate or the like stored therein, which makes it possible to avoid a kidney problem, diarrhea, vomiting or the like—which would otherwise be caused due to acidosis or the like—and also to successfully maintain the pH value of the content at a value close to the corresponding body fluid until administration.

The present invention has achieved the above object by providing a medical container with an electrolyte solution stored therein. This medical container comprises:

- a resin-made container main body;
- a base solution compartment arranged in said container main body and filled with said electrolyte solution in a state steam-sterilized together with said container main body;
- at least one isolated compartment or connected compartment arranged in said container main body, isolated from said base solution compartment by an isolation wall interposed therebetween, and filled with a bicarbonate;
- openable means for permitting aseptic communication between said base solution compartment and said isolated compartment or connected compartment by an operation from an outside of said container main body at the time of use, said openable means being formed at at least a part of said isolation wall.

DETAILED DESCRIPTION OF THE INVENTION AND PREFERRED EMBODIMENTS

Figure 1:
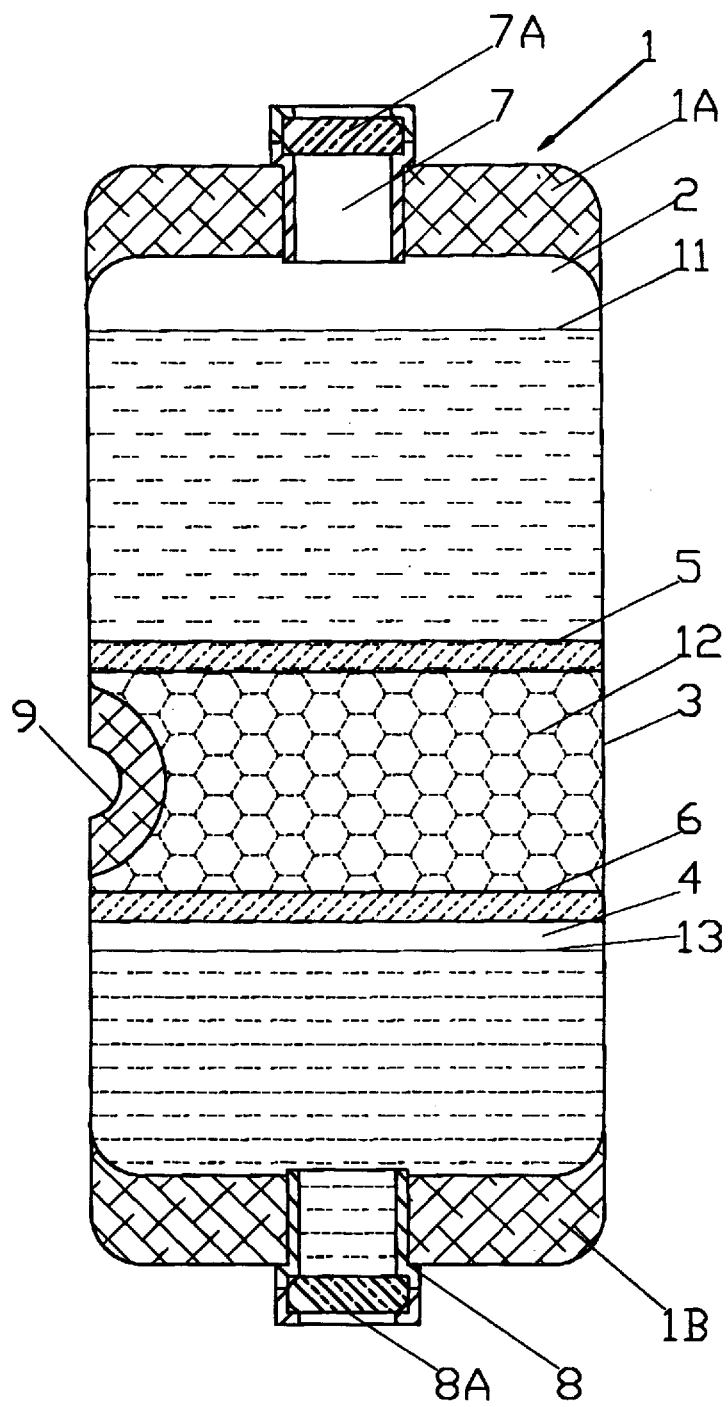
FIG. 1 is a cross-sectional view of a medical container according to a first embodiment of the present invention.

The medical container according to the present invention is provided with the isolated or connected compartment. The bicarbonate is stored in the compartment. This bicarbonate is mixed with the electrolyte solution (i.e., the base solution) when the openable means is opened at the time of use. As a consequence, the electrolyte (i.e., infusion solution, dialysate or organ-preserving solution) which is used for administration, dialysis or the like contains bicarbonate ions at the time of use. When administered, the electrolyte causes no variation in the in vivo concentration of bicarbonate ions and the in vivo pH value remains unchanged. Unlike the conventional medical containers, an electrolyte disorder such as acidosis is not induced. Described specifically, the amount of an electrolyte such as an acetate or a lactate can be reduced in accordance with the proportion of the bicarbonate so that bicarbonate ions are directly introduced into the body to maintain the in vivo concentration of bicarbonate ions constant. Further, the addition of the bicarbonate makes it possible to maintain the pH value within a range of from 6.0 to 8.0. This can prevent a stomach ache, diarrhea or the like which would otherwise be caused by a reduction in pH value at the time of administration.

In the case of an artificial kidney dialysate or peritoneal dialysate, an electrolyte disorder such as acidosis or alkalosis is not developed unlike the conventional dialysates. Owing to the addition of the bicarbonate, the pH of the dialysate can be maintained within a preferred range of from 6.5 to 7.5. This makes it possible to prevent a reduction in immunocompetence which would otherwise occur due to a stomach ache or an abnormal pH value in dialysis, whereby infectious diseases can be reduced.

The bicarbonate is stored in the form of powder, granules or tablets, especially as powder in the compartment in the container. Unlike the conventional bicarbonate solution, it therefore does not undergo easy decomposition even when stored over a long time. Especially even when sterilized under radiation, the bicarbonate remains free from such a potential problem that it may be decomposed to result in the formation of an electrolyte solution of a composition different from the desired one. If the sterilization under radiation is electron-beam sterilization by a low or medium voltage apparatus, facilities are economical and can be converted into a mass-production line with extreme ease.

The bicarbonate is filled in the isolated or connected compartment which is separated from the base solution compartment. A portion of an electrolyte in the electrolyte solution can be provided in the form of the bicarbonate of an alkali metal, and this bicarbonate can be filled in the form free from decomposition into carbon dioxide gas. Since the electrolyte is partly added as the bicarbonate salt of the alkali metal, for example, sodium or potassium bicarbonate in the isolated or connected compartment, the pH value of the electrolyte solution which contains a saccharide or the like can be set low, thereby making it possible to stably maintain the saccharide or the like during autoclave sterilization. In addition, once calcium ions react with bicarbonate ions, calcium bicarbonate is formed. This calcium bicarbonate is hardly soluble. However, the electrolyte solution is maintained in an acidic state so that the precipitation of the insoluble calcium salt does not take place during storage. When the carbonate is mixed with the base solution, the carbonate dissolves gradually. Formation of the calcium bicarbonate precipitate can therefore be avoided practically. Formation of a precipitate or the like can therefore be avoided practically.

At the time of use, the bicarbonate is mixed in an aseptic state with the electrolyte solution so that the medical container can provide a suitable infusion solution, dialysate or organ-preserving solution.

In the medical container according to the present invention, the openable means can be formed of a peelable seal portion or weak seal portion separable from the outside of the container main body. A user of the medical container can therefore make the compartments communicate with each other with extreme ease. Upon fabrication of the medical container, sanitary line processing is feasible. The medical container easily permits mass production.

In the medical container according to the present invention, the container main body can be equipped with an inner layer made of a blend of polyethylene and polypropylene. This makes it possible to easily form the pealable seal portion in the container main body. The pealable seal portion or weak seal portion has such seal strength that it can be separated from the outside. Specifically, such a seal portion can be separated when a pressure produced upon pressing the container main body reaches a range of from 0.02 to 0.15 kgf/cm$^2$.

In the medical container according to the present invention, the isolated compartment or connected compartment has preferably been subjected to radiation sterilization by γ rays, electron beams or ultraviolet rays. This can easily sterilize the bicarbonate. Further, the bicarbonate is absolutely free from the potential problem of a quality modification by such radiation because the bicarbonate has a simple salt structure. Moreover, the medical container is not exposed to high-pressure steam or the like. The medical container is therefore free from the problem that water or the like may penetrate through the wall of the container, so that the bicarbonate scarcely undergoes chemical decomposition.

In the medical container according to the present invention, the radiation sterilization of the isolated compartment or connected compartment can be electron beam sterilization at an accelerating voltage of 1 MeV or lower, and the isolated compartment or connected compartment can be equipped with a wall having a thickness of from 10 to 1,600 μm. This allows an electron beam irradiation apparatus to surely sterilize the bicarbonate in the isolated or connected compartment through its wall even at an accelerating voltage of 1 MeV or lower. Unlike X-rays or the like, this apparatus does not require any large shield. For the mass production of the medical container, a fabrication line can therefore be constructed in a compact form.

In the medical container according to the present invention, the radiation sterilization of the isolated compartment or connected compartment can be ultraviolet ray sterilization, and the isolated compartment or connected compartment can be equipped with a wall having a thickness of from 10 to 100 μm, an ultraviolet transmission of at 60% or higher at a wavelength of 250 nm when the thickness is 10 μm, and a density of from 0.95 to 0.85 g/cm$^3$. These features make it possible to easily sterilize the bicarbonate in the compartment by a simple facility such as an ultraviolet ray apparatus.

In the medical container according to the present invention, communication of the base solution compartment with the isolated compartment or connected compartment can preferably result in mixing of the electrolyte solution and the bicarbonate into an infusion solution. The infusion solution has a pH in a range of from 5.5 to 7.5 and an $HCO_3^-$ at a concentration of from 1 to 65 mEq/l.

In the medical container according to the present invention, communication of the base solution compartment with the isolated compartment or connected compartment can preferably result in mixing of the electrolyte solution and the bicarbonate into a peritoneal dialysate containing:

an $HCO_3^-$ at a concentration of from 1 to 40 mEq/l,
an $Na^+$ at a concentration of from 90 to 150 mEq/l,
a $Ca^{2+}$ at a concentration of from 0 to 6 mEq/l,
an $Mg^{2+}$ at a concentration of from 0 to 3 mEq/l,
a $Cl^-$ at a concentration of from 90 to 135 mEq/l,
a $CH_3COO^-$ or $CH_3 CH(OH)COO^-$ at a concentration of from 0 to 40 mEq/l, and
one or more of saccharides; and having:
an osmotic pressure in a range of from 300 to 680 mOsm/l, and
a pH in a range of from 5.7 to 7.5.

In the medical container according to the present invention, communication of the base solution compartment with the isolated compartment or connected compartment can preferably result in mixing of the electrolyte solution and the bicarbonate into an organpreserving solution containing:

an $HCO_3^-$ at a concentration of from 1 to 50 mEq/l; and having:
an osmotic pressure in a range of from 250 to 400 mOsm/l, and
a pH in a range of from 3 to 10.

In the above medical container, the pH value of the electrolyte solution is maintained at 5.5 or lower in the base solution compartment even when a saccharide or the like is contained in the electrolyte solution. Further, the pH of the electrolyte in the container after opening the openable means can readily maintained in a range of from 6.0 to 8.0. Accordingly, the saccharide in the container is prevented from discoloration or a quality modification during autoclave sterilization. When used for a patient, the resultant infusion solution or the like does not cause a stomach ache or the like because its pH value has not been lowered. Further, the bicarbonate in the above medical container can be the sodium salt or the potassium salt. In this case, a sodium or potassium component for the electrolyte can be added in an amount smaller by its amount in the bicarbonate, so that the pH of the electrolyte solution which is hermetically stored in the base solution compartment can be readily maintained at 5.5 or lower until its use. Even if calcium or magnesium ions are contained in a small amount on a side of the electrolyte solution, the bicarbonate is progressively dissolved into the whole electrolyte solution subsequent to the opening of the openable means. The medical container therefore scarcely form a precipitate or the like.

Next, the medical container according to the first embodiment of the present invention will be described with reference to FIGS. 1 through 4 of the accompanying drawings.

The medical container according to this embodiment, which is designated at numeral 1, is a medical container which stores therein an electrolyte solution for use as a solution to be administered into the body, especially a medical container of a total parenteral nutrition which is composed of a hypertonic saccharide solution and is administered through a central vein route. The medical container is internally divided into three compartments 2,3,4. A partition wall between the compartment 2 and the compartment 3 as well as another partition wall between the compartment 3 and the compartment 4 are wholly formed of pealable seal portions 5,6 which can be opened from an outside of the container to communicate the associated compartments with each other. The first compartment 2 stores therein a first infusion component 11 such as an electrolyte solution. The first infusion component 11 has been subjected to autoclave sterilization subsequent to its filling in the first compartment 2. The second compartment 3, on the other hand, stores therein a bicarbonate 12 which has been subjected to radiation sterilization subsequent to its filling.

The infusion solution in the present embodiment will be described in further detail. The medical container 1 according to this embodiment is formed of a thermoplastic resin wall. Heat-sealed portions 1A,1B are formed at opposite ends of a tubular resin sheet, whereby a container main body is formed. Further, two pealable seal portions 5,6 which are pealable from the outside are formed in an intermediate section of the container 1 at different locations, respectively. By the pealable seal portions 5,6, the container 1 is divided into the first compartment 2, the second compartment 3 and the fourth compartment 4.

The heat-sealed portion 1A,1B are provided with a filling/delivery port 7 and a filling port 8, respectively. The first compartment 2 is filled with the first infusion component 11 in the autoclave-sterilized state. Further, an drug-filling indentation 9 is formed in a side edge of the second compartment 3. The second compartment 3 is filled with the bicarbonate 12 in the radiation-sterilized state.

A thermoplastic sheet which is employed in the medical container 1 according to this embodiment is made of linear low-density polyethylene. The tubular resin sheet has been formed by blown film extrusion. In the present invention, the material is not limited to linear low-density polyethylene, but a variety of resins known per se in the art can be used insofar as they are thermoplastic resins. For example, it is possible to use a material having high flexibility such as a low-density polyethylene resin, a high-density polyethylene resin, a polypropylene resin, a soft polyester resin, a chlorinated polyethylene resin, a vinyl chloride resin, or an ethylene-vinyl acetate copolymer. However, as a resin having little adverse effects on the infusion components 11,12, 13 and the like, use of an olefin resin as in this embodiment is preferred.

In the present invention, the resin sheet wall of the medical container can also be in the form of a multilayer laminate of different resins. In this case, it is desired to use a resin having extremely low $CO_2$ permeability especially for an outer layer, an intermediate layer or the like. When a resin layer of such high $CO_2$ barrier property is arranged, release of carbon dioxide gas from the compartment 3 of the container 1 through the resin sheet is extremely unlikely so that the long-term stable storage in the resin can be assured further. Examples of such a resin can include high-density polyethylene, polyvinylidene chloride, polyesters, nylon, vinylon, and the like.

In the present invention, the medical container is not necessarily limited to a blow-film extrusion product but can be an extrusion product, a vacuum-formed product, an injection molded product, a blow-molded product or the like.

The medical container 1 according to this embodiment is formed 500 mm long and 200 mm wide. The container wall is formed 200 $\mu$m thick. In the present invention, the wall thickness of the medical container 1 can desirably be from 1600 to 10 $\mu$m, notably from 800 to 30 $\mu$m. If the thickness of the container wall exceeds the above range, it will become difficult to perform radiation sterilization of the bicarbonate 12 by a simple electron beam irradiation apparatus which will be described subsequently herein. This will make it difficult to fabricate the medical container by a mass production line. On the other hand, a wall thickness smaller than the above range will inconveniently lead to more frequent container wall ruptures.

Figure 4:
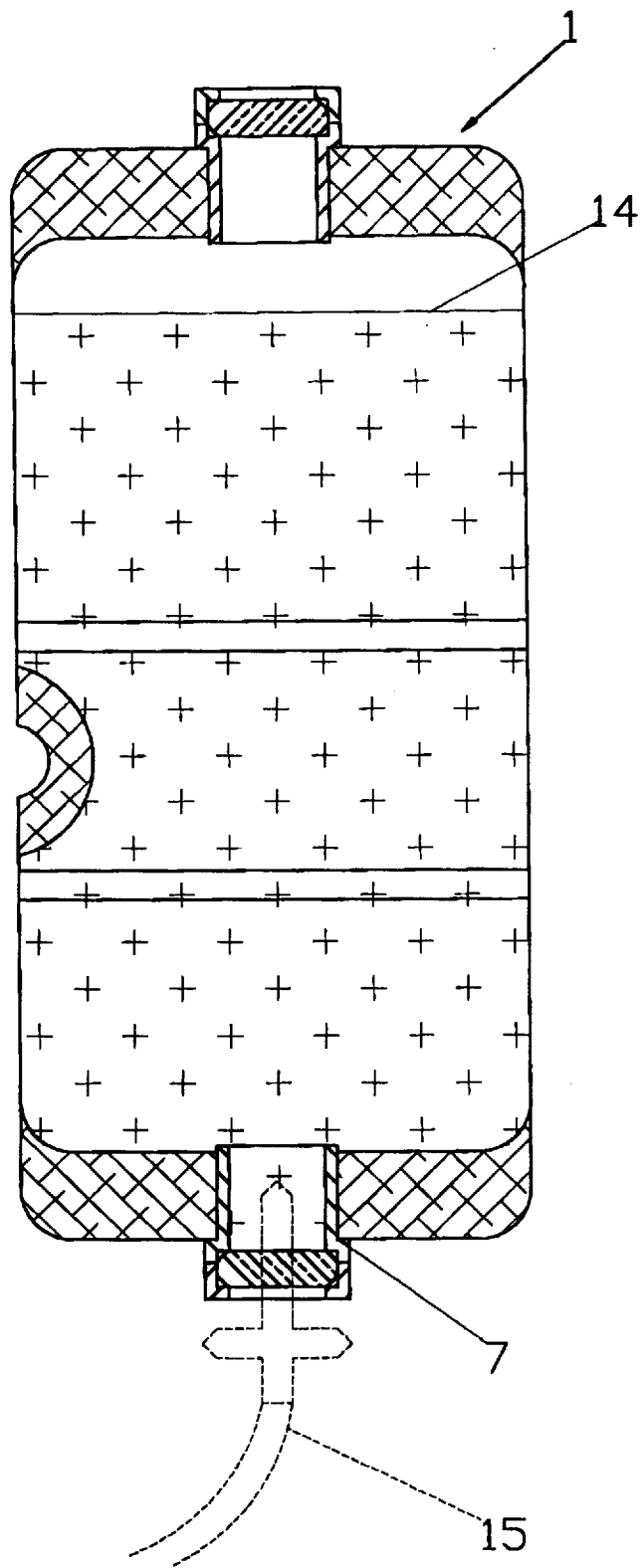
FIG. 4 is a cross-sectional view of the medical container according to the first embodiment in use.

As is illustrated in FIG. 4, mixing of the infusion components 11,12,13 results in the formation of a total parenteral nutrition 14.

This total parenteral nutrition 14 is administered through a central vein and contains one or more of saccharides in a range of from 10 to 50 wt.%, especially in a range of from 15 to 30 wt.%. Such an infusion solution is administered for the purpose of replenishment of nutrients to patients subjected to massive abscission of the intestine or patients suffering from small intestinal lesions or severe diarrhea.

As the saccharides, glucose is used primarily. In addition to glucose, fructose, xylitol, sorbitol and the like are also usable.

The total parenteral nutrition 14 also contains electrolytes as needed in addition to the saccharides. Illustrative of such electrolytes are Na (sodium), K (potassium), Cl (chlorine), Ca (calcium), and Mg (magnesium). Further, trace metals such as Zn (zinc), P (phosphorus), Fe (iron) and Cu (copper) and organic acids such as citric acid, gluconic acid, acetic acid (acetates) and lactic acid (lactates) can also be added.

These electrolytes and organic acids are used as hydrochlorides, lactates, acetates, sulfates, phosphates, gluconates, or glycerophosphates. In the case of Ca, it is used as the glycerophosphate. Further, the phosphate of a polyhydric alcohol or a saccharide can also be used to supply P in an amount sufficient to avoid the formation of a precipitate or the like.

Na is used in a form of $Na^+$ at a concentration of from 0 to 160 mEq/l, especially from 20 to 80 mEq/l in the infusion solution. K is used in a form of $K^+$ at a concentration of from 0 to 80 mEq/l, especially from 10 to 70 mEq/l in the infusion solution. Cl is used in a form of $Cl^-$ at a concentration of from 0 to 160 mEq/l, especially from 20 to 80 mEq/l in the infusion solution. Ca is used in a form of $Ca^{2+}$ at a concentration of from 0 to 20 mEq/l, especially from 4 to 15 mEq/l in the infusion solution. Mg is used in a form of $Mg^{2+}$ at a concentration of from 0 to 25 mEq/l, especially from 6 to 20 mEq/l in the infusion solution. P is used at a concentration of from 0 to 500 mg/l, especially from 120 to 350 mg/l in the infusion solution. Zn is used at a concentration of from 0 to 40 $\mu$mol, especially from 5 to 30 $\mu$mol in the infusion solution.

The total parenteral nutrition 14 in this embodiment contains bicarbonate ions at a concentration in a range of from 1 to 65 mEq/l in combination with or in place of an electrolyte such as an acetate or a lactate. The concentration of bicarbonate ions is preferably around their concentration in plasma and are contained especially in a range of from 5 to 50 mEq/l, in particular in a range of from 15 to 30 mEq/l. A bicarbonate ion concentration higher than the above range may involve the potential problem that alkalosis may occur on a patient after administration. A bicarbonate ion concentration lower than the above range, on the other hand, may fail to yield bicarbonate ions in blood by decomposition of an acetate or the like in a hepatopathic or the like, so that acidosis or the like may be developed. Owing to the addition of the bicarbonate ions, it is desired to contain acetate ions or lactate ions at a concentration of 25 mEq/l or lower, or especially for a severe hepatopathic, at a concentration of from 15 to 0 mEq/l.

The total parenteral nutrition 14 is also required to replenish calorie source. It is therefore desired to add, besides the saccharide, an amino acid preparation and a fat emulsion as the remaining two nutrients out of the three major nutrients. In this embodiment, the infusion solution 14 contains an amino acid preparation which induces the Maillard reaction with the saccharide during autoclave sterilization.

The first infusion component 11 consists of a base solution of the saccharide and the electrolytes. The bicarbonate is however excluded from the infusion component 11 because the bicarbonate 12 is filled in the second compartment 3. Further, the bicarbonate 12 is an alkaline salt so that the alkaline salt also substitutes for a portion of a salt to be included in the first or second infusion component 11 or 13. As the salt, it is preferred to use such a salt that can be readily dissolved when the bicarbonate 12 is mixed in the infusion component 11. The sodium salt or potassium salt is preferred as such a salt. In this case, the amount of sodium or potassium used as the bicarbonate 12 should be subtracted from an amount in which sodium or potassium would otherwise have to be contained in the infusion component 11.

The pH value of the infusion component 11 in the first compartment 2 is lowered to 5.5 or further. Especially in the present embodiment, the pH value is controlled to a range of from 5.0 to 3.0. A pH value of the infusion component 11 higher than the above range may cause discoloration or a quality modification of the saccharide during its autoclave sterilization. Further, the overall pH value of the total parenteral nutrition 14 is desirably in a range of from 6.0 to 8.0, especially from 6.5 to 7.5. A pH value of the infusion solution 14 lower than the above range leads to frequent developments of diarrhea, a stomach ache or the like on patients, whereas a pH value of the infusion solution (total parenteral nutrition) 14 higher than the above range has the potential problem of alkalosis. Accordingly, if the pH value of the infusion component 11 becomes lower than 3.0, the overall pH of the resulting total parenteral nutrition 14 is low even immediately after the infusion component 11 and the bicarbonate 12 are mixed together,. Such total parenteral nutrition has the potential problem that it may give adverse effects to a patient.

The bicarbonate 12 is powder of sodium bicarbonate in this embodiment. The bicarbonate 12 can be in the form of powder, granules, tablets or a suspension in the present invention. For its stability, however, a solid form such as powder is preferred. Although the bicarbonate can be any salt other than the sodium salt, the sodium salt and the potassium salt are particularly desired. Each of them is readily soluble in the infusion components 11,13 so that it can be satisfactorily added as an electrolyte component. To the second compartment 3, one or more carbonates, hydroxides and/or the like can also be added as needed besides the bicarbonate 12.

In this embodiment, sodium bicarbonate is used in an amount sufficient to have bicarbonate ions contained at a concentration of 24 mEq/l in the resulting total parenteral nutrition 14. Since the first infusion component 11 and the second infusion component 13 are contained in a total amount of 1000 ml in the container 1, sodium bicarbonate as the bicarbonate 12 is used in an amount of 2.02 g.

The thickness of the second compartment 3 with the bicarbonate 12 filled therein can desirably be 3,200 $\mu$m or less, especially 1,600 $\mu$m, including the thickness of the container wall. When the second compartment 3 is radiation-sterilized from both sides, the radiation sterilization can be readily performed by a simple electron beam sterilization apparatus to be described subsequently herein provided that the thickness of the second compartment 3 is within the above range.

The second infusion component 13 is an amino acid preparation. This amino acid preparation is added with essential amino acids (E) and non-essential amino acids (N), and their ratio is set at about 1 or so. It is necessary to administer such amino acids in combination with a sufficient amount of a saccharide. The quantity of calorie to be administered per gram of the nitrogen in the amino acids is aimed at 150 to 200 (cal/N). Further, a branched-chain amino acid preparation is administered to patients who have fallen into hepatic coma. Such an amino acid preparation can desirably be contained in a proportion of from 0.5 to 15 wt.%, especially from 1 to 10 wt.% in the infusion solution.

Illustrative amino acids can include glycine, L-alanine, L-proline, L-aspartic acid, L-serine, L-tyrosine, L-glutamic acid, L-cysteine, L-leucine, Lisoleucine, L-valine, L-lysine, L-methionine, L-phenylalanine, L-threonine, L-tryptophan, L-arginine, L-histidine. Amino acids can be used not only in the form of free amino acids but also in the form of their inorganic salts, organic salts, biohydrolysable esters, or oligomers like peptides formed of two or more amino acid molecules.

The first infusion component 11 and the second infusion component 13 have been subjected to autoclave sterilization within the first compartment 2 and the third compartment 4, respectively. The autoclave sterilization is conducted based on the standards for steam sterilization as specified in the Pharmacopoeia of Japan. In this embodiment, it is performed at 100 to 130° C. in an autoclave or the like. It is to be noted that any steam sterilization known per se in the art can be adopted in the present invention.

The bicarbonate 12 has been subjected to radiation sterilization within the second compartment 3. In this embodiment, the radiation sterilization inside the second compartment 3 was performed by electron beam radiation sterilization. The radiation sterilization in this invention can be effected under $\gamma$ rays, electron beams or ultraviolet rays. However, from the standpoint of the sureness and economy of sterilization and the applicability to mass production, desired is electron beam radiation sterilization which will be described hereinafter.

To assure complete electron beam radiation sterilization, the transmission of an electron beam through the container wall is critical. The transmission of an electron beam is primarily determined by an accelerating voltage. In the case of a high-energy accelerating voltage apparatus, the transmission is 13,000 g/m$^2$ max. This is equivalent to 13,000 $\mu$m in terms of the thickness of water (specific gravity: 1 g/cm$^3$). Use of a larger accelerating voltage apparatus however requires a larger shield for X-rays, and also involves the potential problem that the resin material may be modified. A 1 MeV or lower accelerating voltage apparatus of the medium to low energy type, especially a 500 KV or lower accelerating voltage apparatus of the low energy type is therefore desired. The transmission is about 1,500 g/m$^2$ max. in the case of a medium-energy model and about 800 g/m$^2$ max. in the case of a low-energy model. Accordingly, 1,600 μm are considered to be an optimal maximum thickness which permits transmission of an electron beam in the case of a resin material. The thickness of the wall of the container 1 and that of the wall of the second container 3 should desirably fall within the above-described range.

Electron beam sterilization is substantially free from a release of X-rays or the like while providing an electron beam with a predetermined degree of penetration insofar as its accelerating voltage is lower than 1 MeV, especially a low-energy accelerating voltage apparatus of 500 KV to 50 KV is employed. No shield is therefore needed for such X-rays or the like, thereby making it possible to arrange electron beam sterilization facilities in a production line without taking much space. Specifically, the penetration of an electron beam at an accelerating voltage of 500 KV is about 800 $g/m^2$ or less so that sufficient penetration is assured especially through a thin resin portion of 800 μm or smaller.

Figure 3:
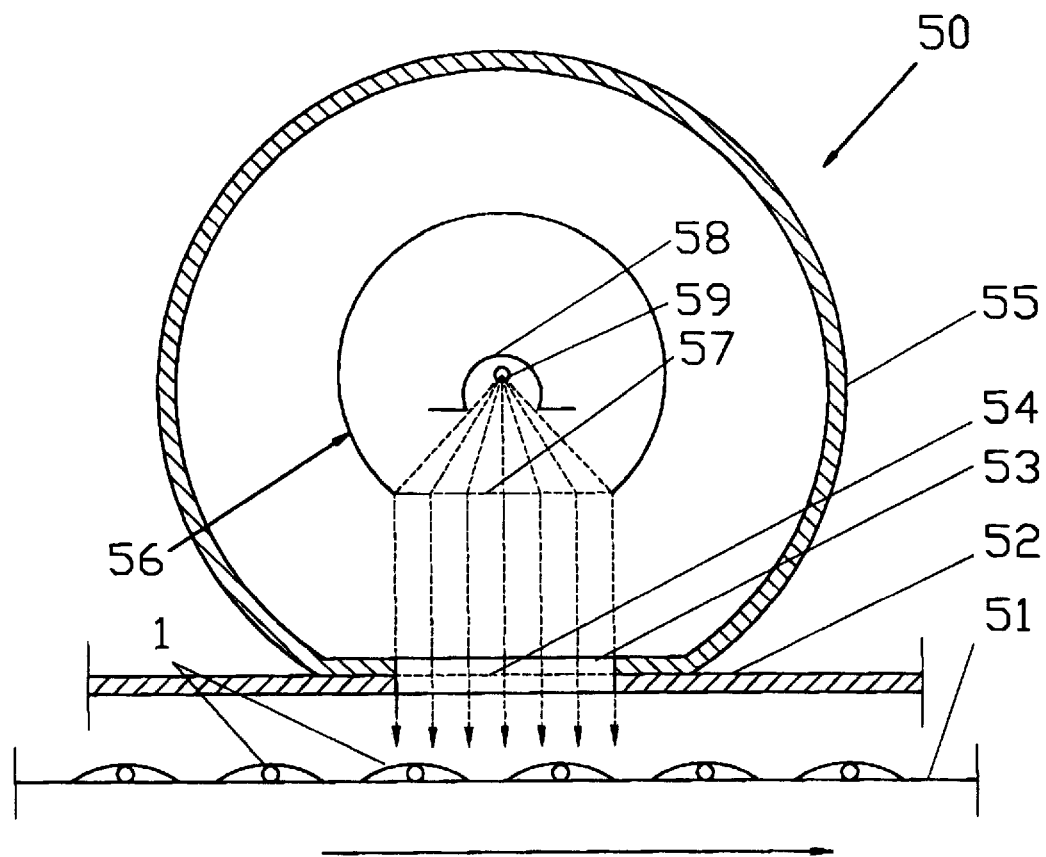
FIG. 3 is a simplified schematic cross-sectional view of an electron beam irradiation apparatus useful for the medical container according to the first embodiment.

As is illustrated in FIG. 3, a electron beam irradiator 50 is arranged over a belt conveyor 51 and is constructed of a base frame 52, a window frame 53 formed in the base frame 52, a window foil 54 attached to the window frame 53, an accelerating tube 55 extending above and over the window frame 53, and an electron beam generating unit 56 accommodated in a vacuum chamber which is in turn formed inside the accelerating tube 55. The electron beam generating unit 56 is composed of a grid 57, a gun frame 58 and a filament 59.

A current is caused to pass through filament 59. The filament 59 is hence heated to generate thermoelectrons. These thermoelectrons are accelerated between the filament 59 and the grid 57 across which a predetermined voltage is applied, whereby electron beams are irradiated from the window foil onto the conveyor 51. Incidentally, the base frame 52 is provided with a lead shield to prevent external leakage of X-rays or the like which are secondarily produced by the irradiation of electron beams.

The quantity of electron beams to be irradiated can therefore adjusted depending on the speed of the conveyor 51 and the quantity of a current to be passed through the filament 59. Further, the penetration of electron beams is also adjustable relying upon the accelerating voltage.

In FIG. 3, it is only the second compartment 3 of the medical container 1 that is under radiation sterilization by the electron beam irradiator 50. In addition, irradiation of electron beams is effected from both sides of the container 1.

In the sterilization of a microorganism, the D value at about 0.2 Mrad (2 kGy) of B. pumilus (spores) E-601 as a standard among ray fungi is referred to as disclosed in Japanese Patent Laid-Open No. 16286/1995. Microbial cells on the order of $10^0$ cells per $cm^2$ are generally found. If safety is fully taken into consideration, contamination with microbial cells as many as up to the order of $10^2$ could still be likely. Against $10^2$ microbial cells, the sterilization assurance level (SAL) is $10^{-6}$% in terms of survival rate. Accordingly, the sterilization in this embodiment is conducted by controlling the quantity of a current to be fed to the electron beam irradiator 50 and the speed of the conveyor in such a way that the interior of the second compartment 3 can be sterilized at 6×0.2 Mrad or greater, preferably at 8×0.2 Mrad or greater.

A description will next be made about a process for the fabrication of the medical container 1.

Firstly, a tubular linear low-density polyethylene sheet, which has been obtained by blow-film extrusion, is cut into a blank of predetermined dimensions. The thus-cut blank is fixedly sealed at opposite end portions thereof by heat seals. At this time, the filling/delivery port 7 and the filing port 8 are attached. Next, the two pealable seal portions 5,6 are formed at the predetermined locations in the medical container 1 so that the interior of the container is divided into the first compartment 2, the second compartment 3 and the third compartment 4.

Described specifically, the linear low-density into a tubular blank of 200 μm in wall thickness, 500 mm in length and 200 mm in width. To form into the shape of the container, the blank is then heat-sealed at opposite ends thereof by an impulse sealer ("Autosealer FA-300-5W", trade name; manufactured by Fuji Impulse Co., Ltd.). As sealing conditions, the sealing time is 1.5 seconds and the cooling time is 5 seconds. The pealable seal portions 5,6 are formed by pinching the blank there for a long time with pinching means preheated to 120° to 140° C. so that they can be peeled off. In the present invention, other methods known per se in the art can also been used for the formation of the pealable seal portions.

Next, the first infusion component 11 is filled in the first compartment through the delivery port 7, and the delivery port 7 is hermetically closed by a rubber plug 7A. The third compartment 4 is filled with the second infusion component 13 through the filling port 8. The filling port 8 is closed by a rubber plug 8A. In this state, the above-mentioned autoclave sterilization is applied to the medical container 1, whereby the first infusion component 11 and the second infusion component 13 are sterilized.

Figure 2:
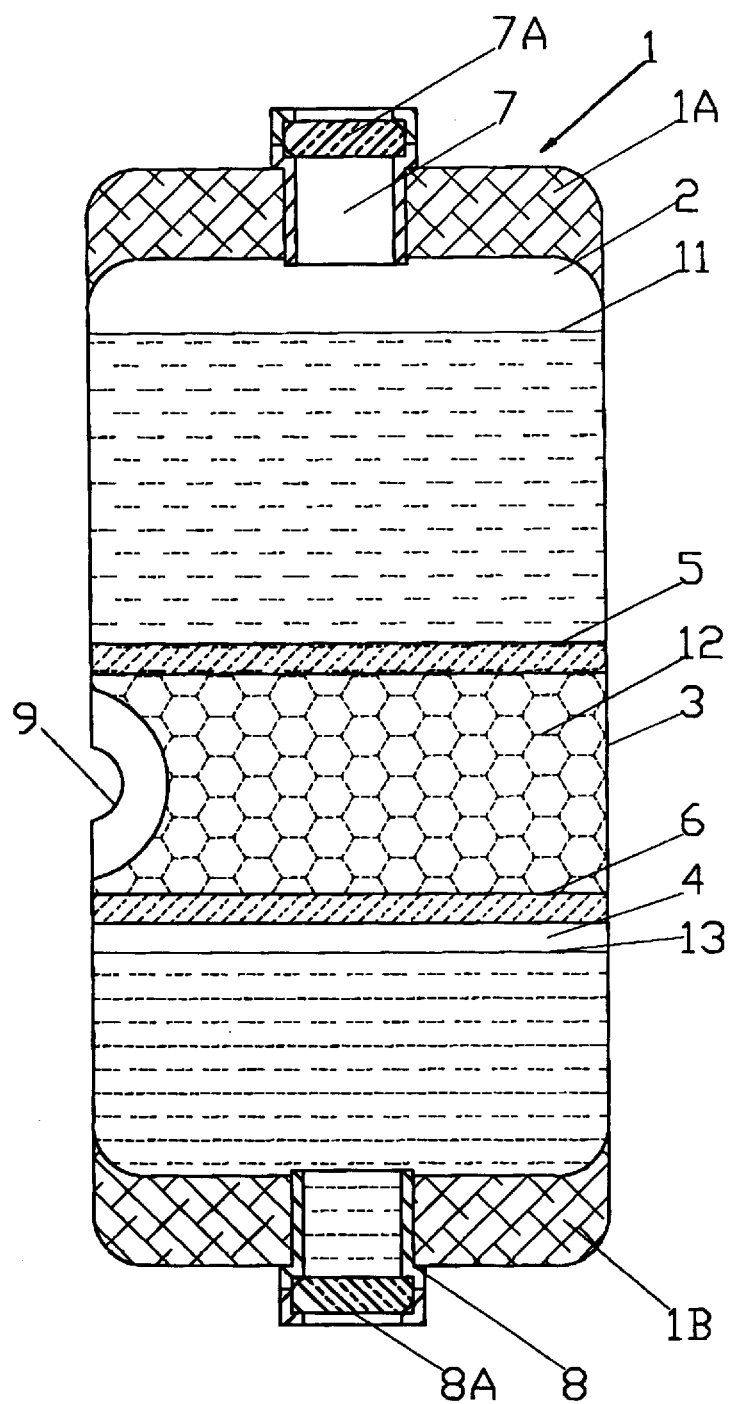
FIG. 2 is a cross-sectional view of the medical container according to the first embodiment of the present invention in the course of its fabrication.

As is illustrated in FIG. 2, the indentation 9 is formed in the second compartment 3 of the medical container 1. Through an opening of the indentation 9, the bicarbonate 12 is filled in the second compartment 3. After the opening of the indentation 9 is heat-sealed, the medical container 1 is conveyed to the electron beam irradiator 50 and is radiation-sterilized both sides of the second compartment 3.

According to the medical container 1 of this embodiment constructed as described above, there is not much potential problem that the bicarbonate 12 could be lost out of the container. Namely, the bicarbonate 12 is not subjected to autoclave sterilization, and is hence free from the potential problem that it could decompose into carbon dioxide gas and could then leak out through the container wall. Further, the bicarbonate 12 is in the form of a solid such as powder and is hardly caused to decompose into carbon dioxide gas or the like. It practically does not decompose in the second compartment 3 especially when it is in the form of powder or granules.

As the bicarbonate 12 is a substance which is free from a problem such as a quality modification or the like during exposure to radiation, radiation sterilization can be conducted through the container wall without any problem or inconvenience. The bicarbonate 12 can be sterilized surely.

Upon application of the medical container 1 to a patient, the pealable seal portions 5,6 are opened from the outside of the container 1 so that all the compartments 2,3,4 are in mutual communication as shown in FIG. 4. The bicarbonate 12 is first dissolved in the second infusion component and is then mixed with the first infusion component which contains calcium or the like therein, whereby the total parenteral nutrition 14 is prepared. In this case, a precipitate of calcium or the like is hardly formed because the bicarbonate 12 is gradually dissolved and mixed in the electrolyte solution containing calcium or the like. Nonetheless, it is desired not to contain calcium in the total parenteral nutrition 14 or the like. A communication needle 15 of an infusion kit is then pierced into the delivery port 7, and infusion of the total parenteral nutrition to the patient is started.

In the total parenteral nutrition with the bicarbonate 12 contained therein, the addition of an acetate, a lactate or the like is minimized as much as possible. This makes it possible to protect an administered patient from acidosis or from electrolyte imbalance which would otherwise be caused by an overdose of an acid. In addition, the pH value of the total parenteral nutrition is controlled at an adequate value in a range of from 6.0 to 8.0, especially from 6.5 to 7.5, the administered patient is not caused to develop such a symptom as a stomach ache or vomiting.

In the embodiment described above, the content of the medical container was the total parenteral nutrition 14. In the present invention, however, the electrolyte solution for infusion can be an initiating solution such as physiological saline, physiological saline-saccharide solution, Ringer solution, Ringer solution-saccharide solution, Hartmann's solution, Hartmann's solution-saccharide solution; an extracellular fluid replenisher solution; a gastric or intestinal juice replenisher solution; an electrolyteretaining solution; or the like. Electrolytes can therefore be used at such a total content as producing an osmotic pressure somewhat higher than that of plasma, and Na can be used in an amount sufficient to yield $Na^+$ ions at a concentration of from 0 to 160 mEq/l.

Next, the medical container according to the second embodiment of the present invention will be described with reference to FIG. 5 through FIG. 8.

As is illustrated in FIG. 5 through FIG. 8, the medical container of this embodiment, which is designated at numeral 21, is a medical container of a dialysate for a circulatory system, namely, a peritoneal dialysate which is composed of a saccharide-containing electrolyte solution and is injected into the abdominal cavity. The medical container 21 is divided into two compartments 22,23. An isolating wall between the compartment 22 and the compartment 23 is partly taken hold of by a clamp 24. The clamp is openable from an outside of the container to communicate the compartments 22 and 23 with each other. The first compartment 22 is filled with a base solution 17 for peritoneal dialysis, which contains an electrolyte solution and has been subjected to autoclave sterilization. The second compartment 23 is filled with a bicarbonate 18 which has been subjected to radiation sterilization subsequent to its filling.

The medical container 21 of the peritoneal dialysate, which pertains to this embodiment, will now be described in further detail. The container 21 is a peritoneal dialysate container which contains a dialysate for acute or chronic peritonitis. Specifically, the container 21 of this embodiment has been formed by stretching a sheet produced by extrusion of high-density polyethylene, cutting the thus-stretched sheet into blanks of predetermined dimensions, placing two of the blanks one over the other, and then completely heat-sealing the blanks along predetermined four sides thereof. A peripheral seal portion 21A and an isolating seal portion 21B are formed in a non-peelable state.

The thermoplastic resin sheet employed for the medical container 21 according to this embodiment is high-density polyethylene. Like the first embodiment, sheets of other known resins can also be used in this embodiment. Laminated multilayer sheets are also usable. Further, the forming process is not necessarily limited to extrusion.

However, as will be described subsequently herein, the interior of the second compartment 23 of the container 21 is sterilized by irradiation of ultraviolet rays. It is therefore desired for the resin sheet to have such properties that its ultraviolet transmission at a wavelength of 250 nm is 60% or higher, especially 70% or higher at a thickness of 10 $\mu$m and its density is in a range of from 0.95 to 0.85 g/cm$^3$. An ultraviolet transmission lower than the above range results in insufficient exposure of the interior of the second compartment 23 to ultraviolet rays. If a resin falls within the above-described density range, it is easier to obtain a resin sheet having an extremely high ultraviolet transmission.

The medical container 21 according to this embodiment is formed 500 mm long and 300 mm wide. The container wall is formed 50 $\mu$m thick. In this embodiment, the wall thickness of the medical 21 container is preferably 100 to 10 $\mu$m, especially 60 to 30 $\mu$m. A wall thickness greater than the above range makes it difficult to perform radiation sterilization of the bicarbonate 18 by an ultraviolet ray irradiator, said radiation sterilization being to be described subsequently herein, so that the medical container 21 can hardly be fabricated by a mass-production line. A wall thickness smaller than the above range, on the other hand, inconveniently leads to more frequent ruptures of container walls.

The isolating seal portion 21B of the container 1 is provided with holes 27,27, in which an isolating clamp 24 is fitted. This clamp 24 is formed of two clamp bars 24A,24B and a hinge 24C. The clamp bars 24A,24B are engageable with each other at free ends thereof remote from the hinge 24C. When the clamp 24 is closed between the holes 27 and 27, the first compartment 22 and the second compartment 23 are completely isolated from each other. On the other hand, opening of the clamp 24 allows the first compartment 22 and the second compartment 23 to communicate with each other.

A peritoneal dialysate 19, which has been formed by mixing the base solution 17 and the bicarbonate 18 together, contains bicarbonate ions at a concentration in a range of from 1 to 40 mEq/l in the electrolyte solution and has a pH in a range of from 5.7 to 7.5.

Further, the bicarbonate 18 is the sodium salt and as electrolytes added in the saccharide-containing base solution 17, are contained $Na^+$ ions in a concentration range of from 90 to 150 mEq/l, $Ca^{2+}$ in a concentration range of from 0 to 6 mEq/l, $Mg^{2+}$ in a concentration range of from 0 to 3 mEq/l, $Cl^-$ in a concentration range of from 90 to 135 mEq/l, and acetate$^-$ or lactate$^-$ in a concentration range of from 0 to 40 mEq/l. The osmotic pressure of the dialysate is from 300 to 680 mOsm/t.

In the first compartment 22, the base solution 17 contains electrolytes and its pH value is maintained at 5.5 or lower. The base solution 17 has been subjected to autoclave sterilization in the first compartment 22. This autoclave sterilization is conducted based on the standards for steam sterilization as specified in the Pharmacopoeia of Japan. In this embodiment, it is performed at 100 to 130° C. in an autoclave or the like. It is to be noted that any steam sterilization known per se in the art can be adopted in the present invention.

In this embodiment, sodium bicarbonate is used at a concentration of 24 mEq/l in terms of sodium bicarbonate ions. As 2,000 ml of the solution are stored in the container 21, the bicarbonate 18 is used in an amount of 4.04 g.

The thickness of the second compartment 23 with the bicarbonate 18 filled therein is desirably 200 $\mu$m or smaller, especially 120 $\mu$m, including the thickness of the container wall. When the second compartment 23 is radiation-sterilized from both sides, sterilization can be easily performed by a simple ultraviolet ray radiation sterilization apparatus insofar as the thickness of the second compartment 23 is within the above range.

The bicarbonate 18 has been subjected to radiation sterilization within the second compartment 23. In this embodiment, the radiation sterilization inside the second compartment 23 was performed by ultraviolet ray radiation sterilization. The radiation sterilization in this invention can be effected under γ rays, electron beams or ultraviolet rays. However, from the standpoint of the possibility of sterilization by an extremely simple apparatus, the economy of sterilization and the applicability to mass production, ultraviolet ray radiation sterilization is desired.

Figure 7:
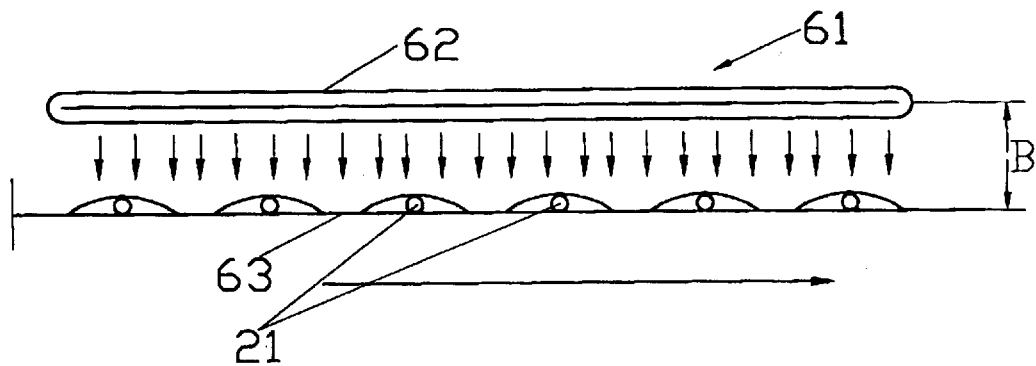
FIG. 7 is a simplified schematic cross-sectional view of an ultraviolet ray irradiation apparatus useful for the medical container according to the second embodiment.

As is depicted in FIG. 7, an ultraviolet ray irradiator 61 is arranged over a belt conveyor 63 and is equipped with high-output ultraviolet lamps 62. These high-output ultraviolet lamps 62 are low-pressure mercury vapor lamps having a high ultraviolet ray intensity around 250–260 nm wavelengths. Desirably, the intensity of ultraviolet radiation is 100 mW/cm$^2$ or more as measured at an irradiating window of the irradiator 61. For this purpose and also for making the irradiator 61 compact, the ultraviolet lamps 62 are desirably of a 200 W to 1 KW range. A distance B (FIG. 7) from the irradiating window to the belt conveyor is 25 mm or less, especially 10 mm or less. When the distance B is 25 mm or less, a quantity of ultraviolet radiation as much as about 70% or more of that at the window can be assured on the surface of the belt conveyor 63.

By the conveyor 63 of the ultraviolet ray irradiator 61, each medical container 21 is conveyed in such a state that it is shielded by an ultraviolet shield or the like except for the area of the second compartment 23. Although not shown in the drawing, an additional ultraviolet ray irradiator is arranged on a downstream side of the ultraviolet ray irradiator 61 so that irradiation of ultraviolet rays can be effected from both the sides of the container 21. The container 21 is treated by turning it upside down between the two ultraviolet ray irradiators.

Incidentally, an exposure dose of approximately 33.3 mW sec/cm$^2$ is considered to be needed for the sterilization of 99.9% of *B subtilis* (spores) which has resistance to ultraviolet rays. By reducing the microbial contamination to the order of $10^{-3}$ per cm$^2$ before the medical container is sterilized, the sterilization of 99.9% (i.e., $10^{-1}$%) assures the sterilization assurance level (SAL) of $10^{-6}$ per cm$^2$. Accordingly, to achieve sterilization in 30 seconds by the ultraviolet ray irradiators 61 in this embodiment, each medical container 21 is treated by controlling the ultraviolet ray irradiators 61 so that ultraviolet radiation reaches the interior of the second compartment 23 in a quantity of at least 1.11 mW.sec/cm$^2$.

Figure 5:
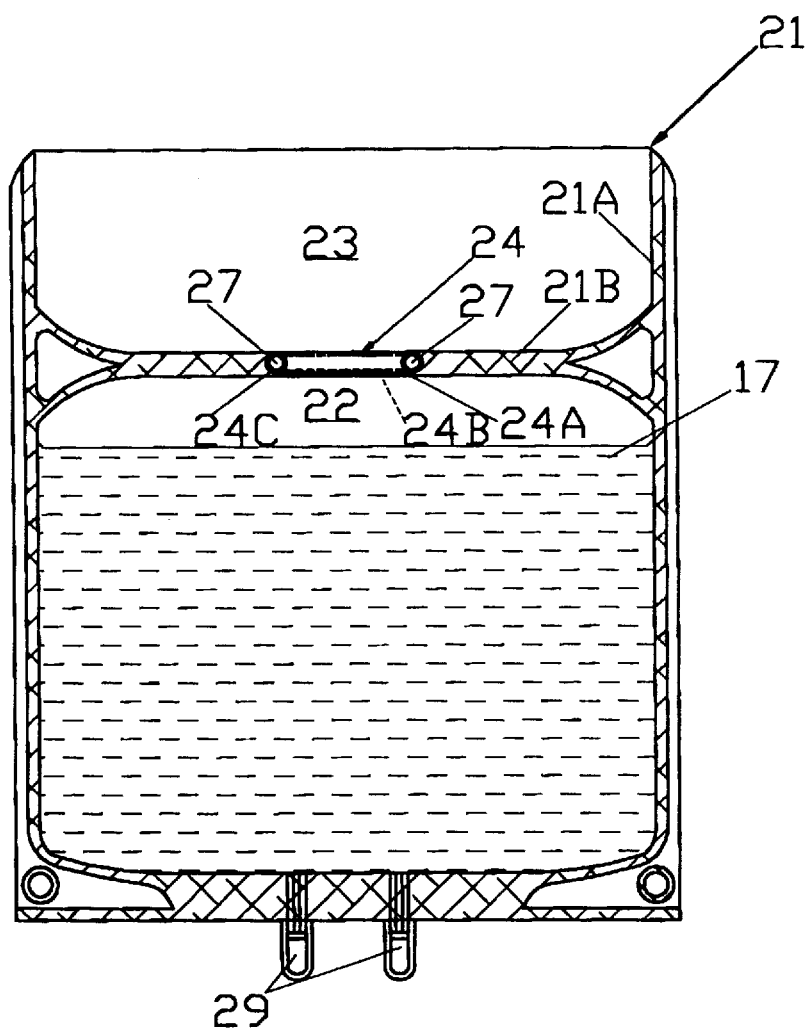
FIG. 5 is a cross-sectional view of a medical container according to a second embodiment of the present invention in the course of its fabrication.
Figure 6:
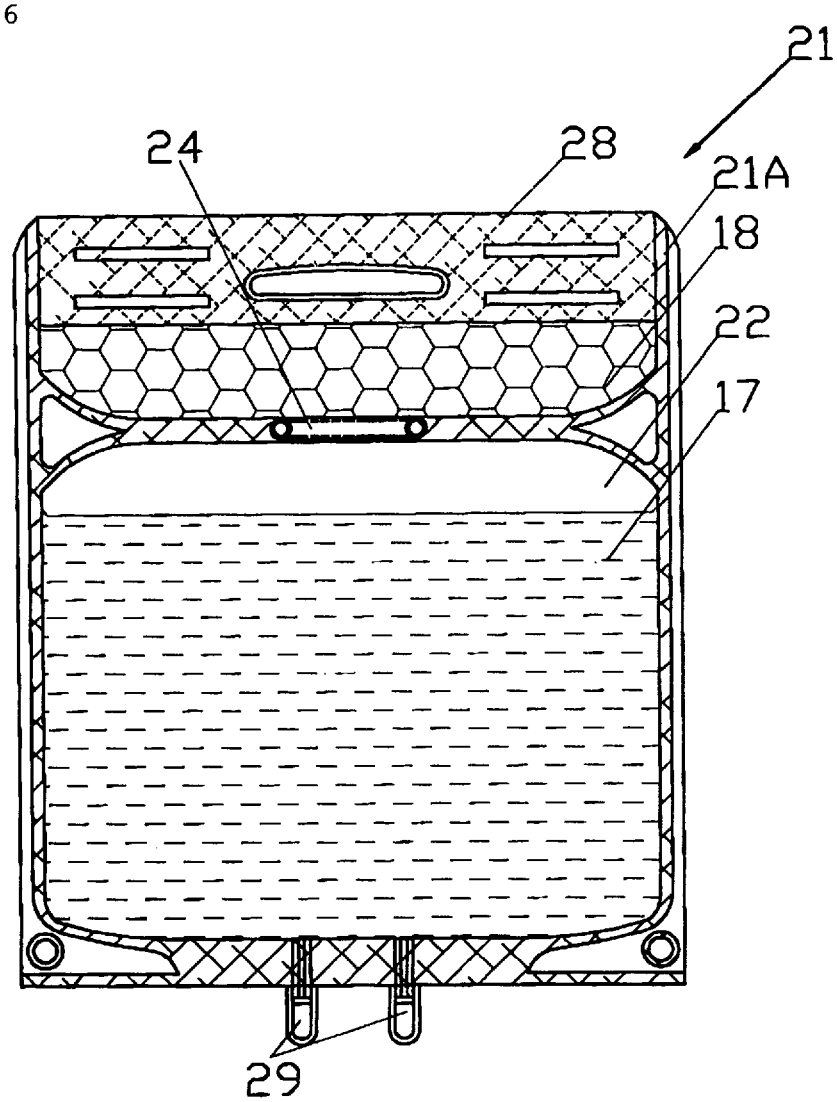
FIG. 6 is a cross-sectional view of the medical container according to the second embodiment.

With reference to FIG. 5, a description will next be made about a process for the fabrication of the medical container 21.

An extruded high-density polyethylene sheet is first cut into blanks of predetermined dimensions. In this embodiment, the high-density polyethylene sheet has a thickness of 50 μm and the blanks are 500 mm in length and 300 mm in width. To form the container shape, two of the thus-cut blanks are then placed one over the other, and by the impulse sealer ("Autosealer FA-300-5W", trade name; manufactured by Fuji Impulse Co., Ltd.), they are completely heat-sealed along their peripheral edges other than the upper edges as viewed in FIG. 5. At this time, delivery ports 29 are attached. As sealing conditions, the sealing time is 1.5 seconds and the cooling time is 5 seconds. Next, the isolating seal portion 21B is formed at the pre-determined location in the medical container 21. The holes 27 are formed in the isolating seal portion 21B. The clamp 24 is fitted in the holes 27, whereby the container 21 is internally divided into the first compartment 22 and the second compartment 23.

The base solution 17 is next filled into the first compartment 22 through one of the delivery ports 29, and the delivery ports 29 are both hermetically capped. In this state, the medical container 1 is subjected to autoclave sterilization as mentioned above so that the base solution 17 is sterilized.

As is shown in FIG. 5, the upper edge of the second compartment 23 of the medical container 21 is left open. Through the open edge, the bicarbonate 18 is filled in the second compartment 23. After the open edge of the second compartment 23 is heat-sealed, the medical container 21 is conveyed to the ultraviolet ray irradiator 61 and the second compartment 23 is radiation-sterilized from both the sides thereof.

In the medical container 21 of the peritoneal dialysate according to this embodiment constructed as described above, there-is not much potential problem that the bicarbonate 18 could be lost out of the container. As the bicarbonate 18 is a substance which is free from a problem such as a quality modification or the like during exposure to ultraviolet rays, ultraviolet ray radiation sterilization can be conducted through the container wall without any problem or inconvenience. The bicarbonate 18 can be sterilized surely.

Figure 8:
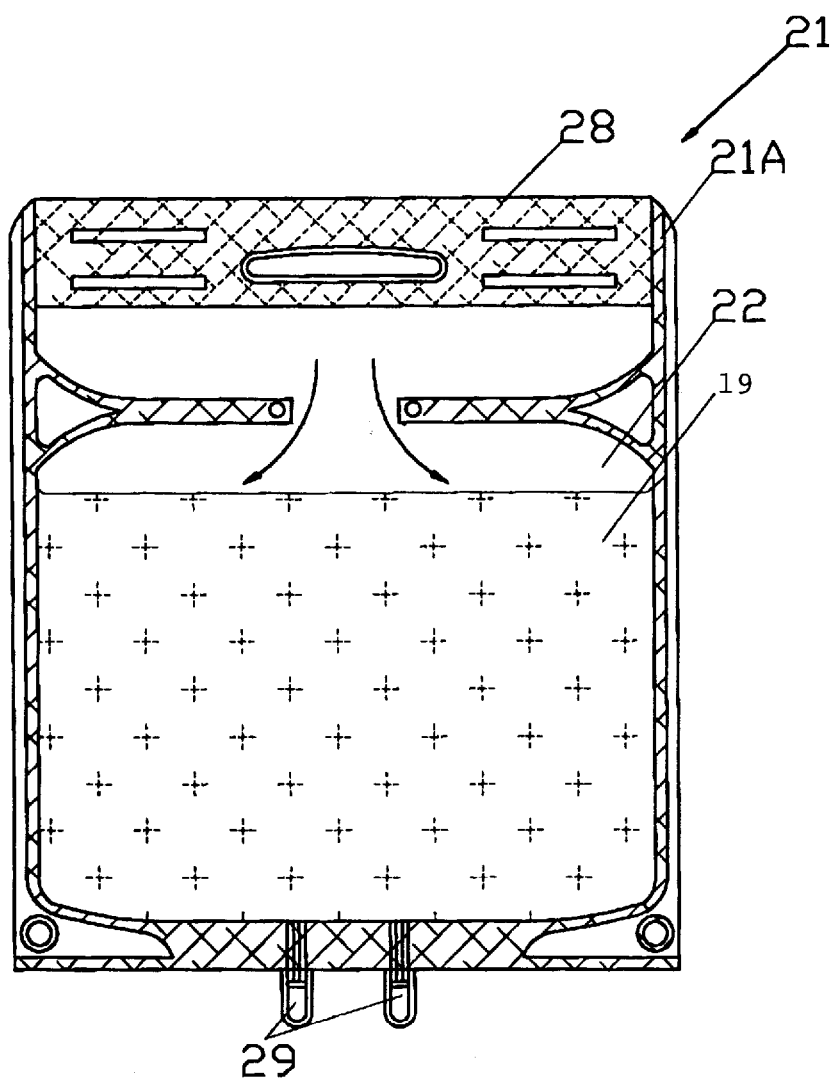
FIG. 8 is a cross-sectional view of the medical container according to the second embodiment in use.

Upon use of the medical container 21 of the peritoneal dialysate, the clamp 24 is released from an outside of the container 21 so that the first compartment 22 and the second compartment 23 are communicated with each other as shown in FIG. 8. The base solution 17 and the bicarbonate 18 are hence mixed together so that the peritoneal dialysate 19 is formed in the container 21. When mixed with the base solution 17, the bicarbonate 18 raises the pH value of the base solution 17 and as a consequence, also serves to regulate the pH of the dialysate 19. Accordingly, an aseptically-pH-regulated peritoneal dialysate can also be prepared in the container 21 at home.

When applying it to a patient, a communication needle such as catheter is pierced through one of the delivery ports 29 of the container 21. The catheter is connected to the abdominal cavity of the patient. The dialysate 19 in the container 21 flows into the abdominal cavity to perform dialysis.

In this case, the concentration of bicarbonate ions in the dialysate 19 is not different from that of bicarbonate ions in the body fluid of the patient. The dialysate 19 is therefore free from the potential problem that bicarbonate ions would flow out from the body fluid into the dialysate to cause acidosis. Further, the control of the concentration of bicarbonate ions can also prevent alkalosis or the like and electrolyte imbalance.

In this embodiment, the peritoneal dialysate 19 was used as the content of the medical container 21. In this invention, the content is not necessarily limited to such a dialysate, and the medical container 21 can also be effectively applied to an artificial kidney perfusate, an artificial kidney dialysate, an artificial kidney replenisher solution, or the like.

Next, the medical container according to the third embodiment of the present invention will be described with reference to FIG. 9.

Figure 9:
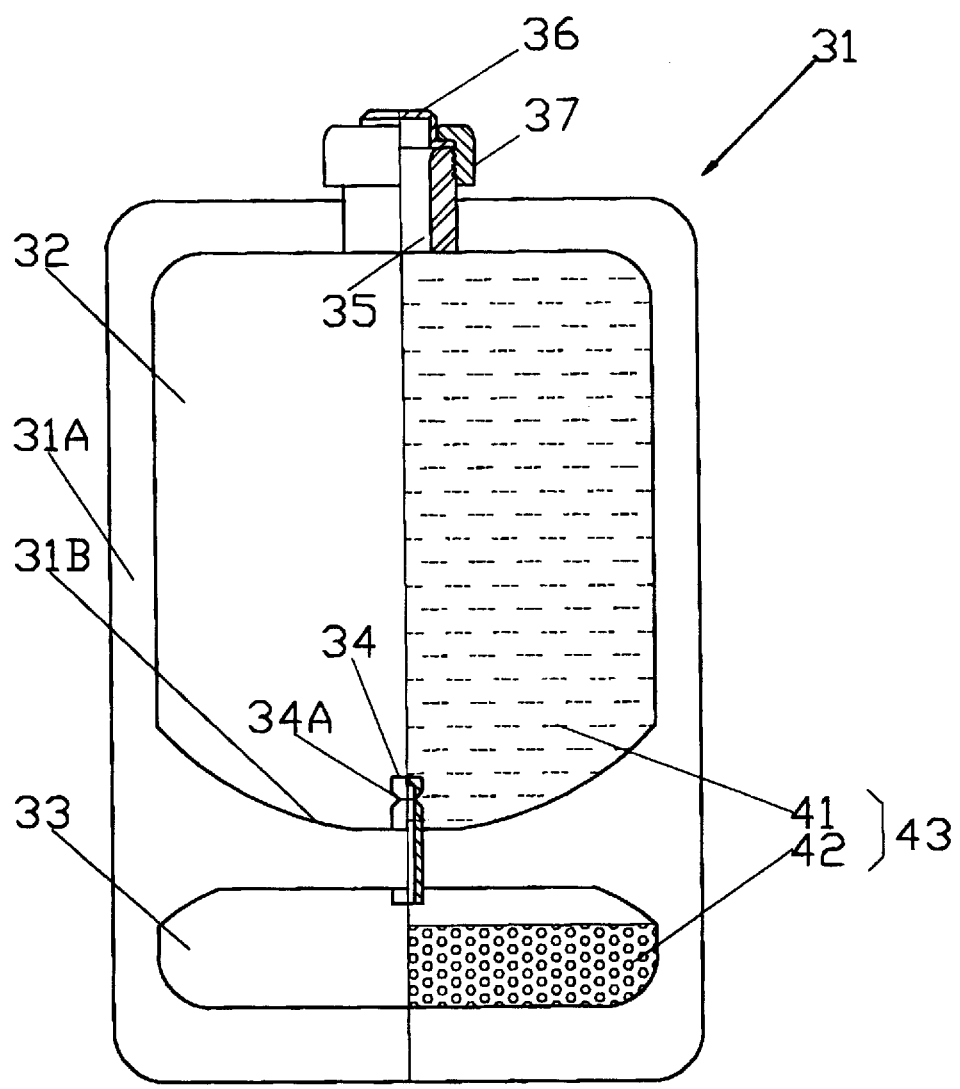
FIG. 9 is a half cross-sectional view of a medical container according to a third embodiment of the present invention.

As is illustrated in FIG. 9, the medical container of this embodiment, which is designated at numeral 31, is a medical container with an organpreserving solution stored therein. This solution is useful for preserving an organ in an immersed state upon transplanting the organ. The medical container 31 is divided into two compartments 32,33. A portion of an isolating wall between the compartment 32 and the compartment 33 is formed of a "click chip" 34 which can cancel the isolation from an outside of the container to communicate the compartments 32 and 33 with each other. An organ-preserving base solution 41 which contains an electrolyte solution is stored in a steam-sterilized state in the first compartment 32, while a bicarbonate 42 which has been subjected to γ-ray radiation sterilization subsequent to its filling is stored in the second compartment 33.

The medical container 31 of the organ-preserving solution according to the present embodiment will be described in further detail. The container 31 is a medical container with the organ-preserving solution stored therein. In this embodiment, the container 31 has been formed specifically by stretching a sheet produced by extrusion of linear low-density polyethylene, cutting the thus-stretched sheet into blanks of predetermined dimensions, placing two of the blanks one over the other, and then completely heat-sealing the blanks along predetermined four sides thereof. A peripheral seal portion 31A and an isolating seal portion 31B are formed in a non-peelable state.

The medical container 31 according to this embodiment is formed 500 mm long and 300 mm wide. The container wall is formed 300 μm thick.

Upon formation of the isolating seal portion 31B, the click chip 34 is attached in a liquid-tight fashion between the two blanks. Normally, the click chip 34 maintains the compartment 32 and the compartment 33 isolated with each other unless the click chip 34 is snapped off. Namely, the click chip 34 is made of a resin and is in the form of a tube closed at one end thereof. When a closed end portion of the click chip 34 is snapped off at a notch 34A formed in a side wall of the closed end portion, the click chip 34 becomes a tube fully opened at opposite ends thereof. At the time of formation of the peripheral seal portion 31A, a delivery port 35 is attached. The delivery port 35 is provided with a cap 36, which seals the delivery port 35 in a liquid-tight fashion by means of a stopper 37.

An organ-preserving solution 43 as a mixture of the base solution 41 and the bicarbonate 42 in this embodiment is composed of Eurocollins' solution as a base. The bicarbonate 42 and the base solution 41 are separately stored in the compartments 33,32.

The organ-preserving solution 43 which has been formed by mixing the bicarbonate 42 and the base solution 41 together has an osmotic pressure in a range of from 250 to 400 mOsm, preferably from 280 to 350 mOsm. Further, the pH of the organ-preserving solution is set at 3 to 10, especially 4 to 9.

The base solution 41 is filled in the base solution filling compartment 32 which occupies a majority of the container 31. As the bicarbonate 42 is filled in the bicarbonate compartment 33 separately from the base solution filling compartment 32, the base solution 41 is filled as a solution of a composition with potassium omitted as much as the theoretical amount of potassium in potassium bicarbonate as the bicarbonate 42. Further, alkali metal salts such as a sodium salt and a potassium salt, alkaline earth metal salts such as a calcium salt and a magnesium salt, and the like are used in pharmacologically-acceptable ranges in the base solution 41. When a saccharide such as glucose is contained in the base solution 41 filled in the base solution filling compartment 32, its pH is desirably 5.5 or lower, especially 5.3 or lower, with 5.0 or lower being more desired. Such acidification of the base solution 41 has be readily achieved as a consequence of the omission of potassium ions from the base solution filling compartment 32 in an amount equivalent to the amount of potassium in the potassium bicarbonate 42. Insofar as the base solution 41 is maintained at a pH value in the above range, there is an extremely low potential problem that glucose or the like in the base solution 41 could undergo a quality modification, even when the base solution 41 is heattreated by autoclave sterilization.

In the base solution 41, it is possible to incorporate an organ preservative and additives known per se in the art, such as excipients, binders, buffers, isotonic agents, pH regulators, antiseptics, solubilizers and thickening agents, as needed.

Examples of already proposed organ preservatives include antibiotics, physiologically-active proteins (insulin, antiplatelet factors, antidiuretic hormones, and the like), saccharides (glucose, mannitol, and the like), vitamins (vitamin C, vitamin E, and the like), organic acids (lactic acid, citric acid, and the like), nucleic acid bases (adenosine triphosphate, and the like), antihypertensives (calcium antagonists, βadrenocaptive antagonists, angiotensin converting enzyme inhibitors, and the like), and anticoagulants (heparin, and the like). Further, drugs such as the phosphoric diester compounds disclosed in Japanese Patent Laid-Open No. 215801/1995 have also been proposed.

In this embodiment, the base solution 41 has been subjected to autoclave sterilization together with the container 31.

The bicarbonate 42 is filled in the filling compartment 33 of the container 31. Based on the amount of the bicarbonate 42, corresponding cations are omitted in a corresponding amount from the base solution 41. In this embodiment, granular potassium bicarbonate is filled as the bicarbonate 42 in the filling compartment 33.

No particular limitation is imposed on the amount of the bicarbonate 42 insofar as it falls within a pharmacologically-acceptable range. In particular, it is desired to fill the bicarbonate 42 in an amount sufficient to yield bicarbonate ions ($HCO_3^-$) to a concentration in a range of from 1 to 50, especially from 5 to 40, more preferably from 10 to 30 mEq/l in the organ-preserving solution. As the base solution 41 is stored in an amount of 1 l in the base solution filling compartment 32 of the container 31 in this embodiment, the potassium bicarbonate as the bicarbonate 42 is employed in a range of from 0.01 to 5.0 g.

With the bicarbonate 42 stored in the filling compartment 33 of the container 31, only the filling compartment 33 has been subjected to γ-ray sterilization.

Figure 10:
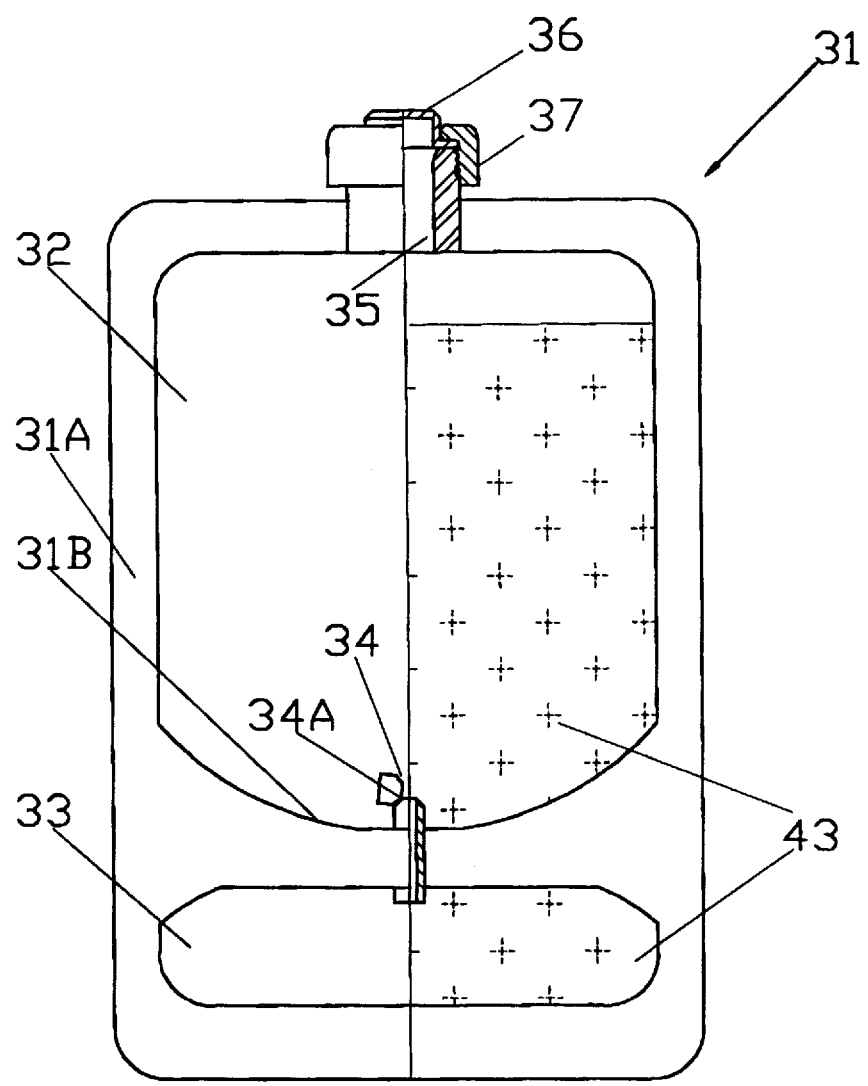
FIG. 10 is a half cross-sectional view of the medical container according to the third embodiment in use.

Upon using the medical container 31 with the base solution 41 and the bicarbonate 42 stored separately therein, the click chip 34 is snapped off from the outside of the container 31 so that the filling compartment 32 and the filling compartment 33 are communicated with each other. Then, as is shown in FIG. 10, the bicarbonate 42 is dissolved in the base solution 41, whereby the organ-preserving solution 43 can be prepared within the medical container 31 by the aseptic operation. A guide tube or the like is then attached to the delivery port 35, and the organ-preserving solution 43 is aseptically filled in a bath in which an organ is placed.

Accordingly, the medical container 31 permits not only storage of the organ-preserving solution 43 for a long period but also application of sure sterilization without relying solely upon sterile filling of the organ-preserving solution 43. Sterility of the organpreserving solution 43 can be fully assured.

The organ preserving solution of this embodiment is used not only for preserving main organs such as liver, kidney, heart and lung, but also for preserving tissues such as cornea.

In each of the first to third embodiments of the present invention, the pealable seal portion, clamp or click chip which is openable from the outside was used as the openable means or the isolation canceling means. Any openable means or isolation canceling means can however be used in the present invention insofar as it is openable from the outside. However, the pealable seal portion is desired from the standpoint of handling and productivity.

Further, the bicarbonate was used in the form of powder or granules in the bicarbonate compartment in each of the first to third embodiments of the present invention. Besides, it can be in the form of a suspension, tablets or the like. Moreover, a non-bicarbonate $HCO_3^-$-yielding substance can be filled in the bicarbonate compartment insofar as its stability is assured.

Figure 11:
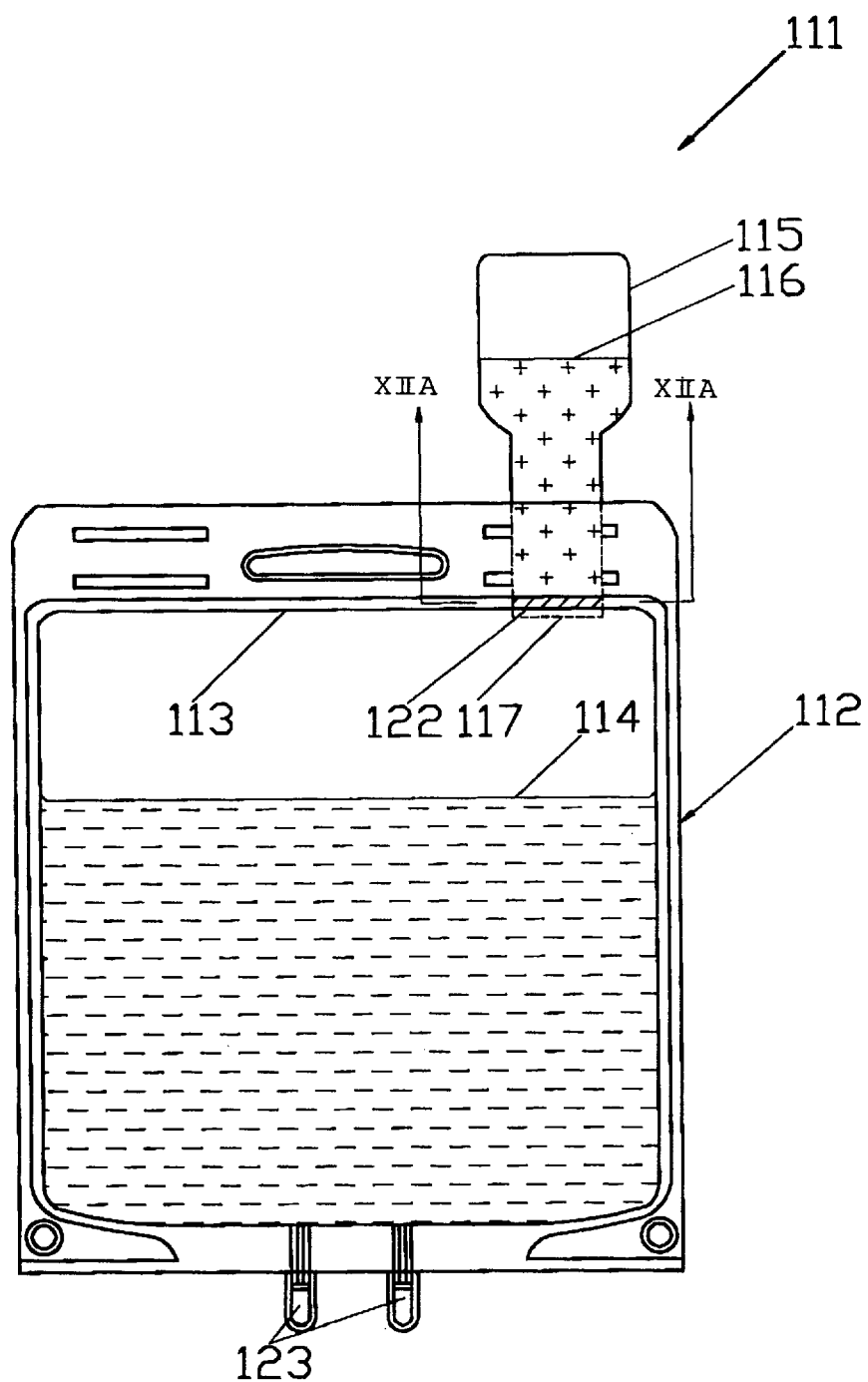
FIG. 11 is a plan view of a peritoneal dialysate container according to a fourth embodiment of the present invention.

Finally, the peritoneal dialysate container according to the fourth embodiment of the present invention will be described with reference to FIG. 11 through FIG. 13. The peritoneal dialysate container according to this embodiment, which is designated at numeral 111, is a container with a peritoneal dialysate stored therein. This peritoneal dialysate is formed of a saccharide-containing electrolyte solution and is injected into the abdominal cavity. The peritoneal dialysate is a solution to be prepared by dissolving a bicarbonate 116 in a base solution 114 which contains a saccharide and electrolytes. A plastic container main body 112, in which the base solution 114 is filled, is provided with a connected container (or connected compartment) in such a way that the latter can be aseptically communicated to the former. The connected container 115 is filled with the bicarbonate 116.

Mixing of the electrolyte solution and the bicarbonate results in the peritoneal dialysate, which contains bicarbonate in a form of $HCO_3^-$ at a concentration of from 1 to 40 mEq/l, sodium in a form of $Na^+$ at a concentration of from 90 to 150 mEq/l, calcium in a form of $Ca^{2+}$ at a concentration of from 0 to 6 mEq/l, magnesium in a form of $Mg^{2+}$ at a concentration of from 0 to 3 mEq/l, chlorine in a form of $Cl^-$ at a concentration of from 90 to 135 mEq/l, acetate or lactate in a form of $CH_3COO^-$ or $CH_3CH(OH)COO$ at a concentration of from 0 to 40 mEq/l, and one or more of saccharides, and which has an osmotic pressure in a range of from 300 to 680 mOsm/l and a pH in a range of from 5.7 to 7.5. In order to form an aseptically-communicable construction between the container main body 112 and the connected container 115, the connected container 115 is communicably connected to the container main body 112, and a seal portion 122 is formed closing up an interior of the connected container 115 and an interior of the container main body 112 therebetween. The seal portion 122 is a pealable seal portion, which is peelable from an outside and permits aseptic communication between the interior of the connected container 115 and that of the container main body 112.

The peritoneal dialysate container 111 according to this embodiment will be described in further detail. The container 111 is a peritoneal dialysate container which contains a dialysate for acute or chronic peritonitis. The container main body 112 of the peritoneal dialysate container 111 is formed of a variable-volume plastic container having flexible walls. In this embodiment, the container main body 112 has been formed specifically by stretching a sheet produced by extrusion of linear low-density polyethylene, cutting the thus-stretched sheet into blanks of predetermined dimensions, placing two of the blanks one over the other, and then completely heat-sealing the blanks along predetermined four sides thereof. A space defined by inseparable seal portions 113 becomes a compartment to be filled with a base solution 114.

Figure 12A:
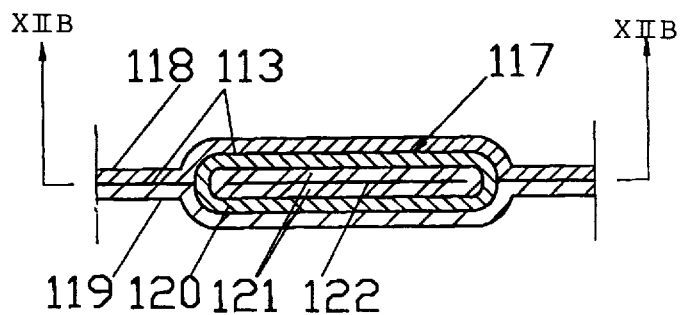
FIG. 12A is a cross-sectional view of a connecting portion between a connected container and a container main body in the peritoneal dialysate container according to the fourth embodiment, taken in the direction of arrows XIIA—XIIA of FIG. 11.
Figure 12B:
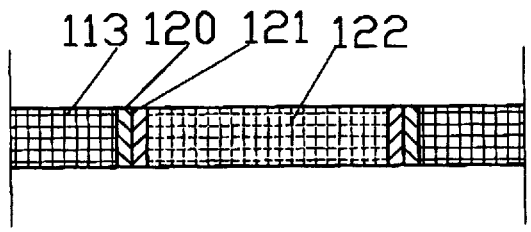
FIG. 12B is a cross-sectional view of the connecting portion between the connected container and the container main body, taken in the direction of arrows XIIB—XIIB of FIG. 12A.

Upon formation of the inseparable seal portions 113 of the container main body 112, the connected container 115 is connected thereto in a communicable fashion. Specifically, as is shown in FIG. 12A, a connecting port portion 117 is inserted and heat-sealed between two blanks 118,119 which forms the container main body 112. The connected container 115 is a blow-molded container and is a multilayer container formed of an outer layer 120 and an inner layer 121. The outer layer 120 is made of a linear low-density polyethylene similar to that of the container main body 112, whereas the inner layer 121 is made of a blend of linear low-density polyethylene and polypropylene. Opposing inner surfaces of the inner layer 121 are not heat-sealed into an inseparable seal portion under heat-sealing conditions of the inner layer 121 or even under temperature conditions for inseparably heat-sealing the container main body 112 and the outer layer 120. Namely, as is illustrated in FIG. 12B, upon formation of the inseparable seal portions 113 on the container main body 112 by a heat sealer or the like, the inseparable seal portions 113 are formed between the two blanks 118,119 of the container main body 112 and also between the outer layer 120 of the connected container 115 and the blank 118,119. On the other hand, the wall of the connecting port portion 117 of the connected container 115 has flexibility and upon formation of the inseparable seal portions, the connecting port portion 117 is caused to collapse so that the opposing surfaces of the inner layer 121 are sealed together into a seal portion but is peelable from the outside.

The composition of the dialysate prepared in both the container main body 112 and the connected container 115 in this embodiment somewhat varies depending on its use, namely, whether it is a continuous ambulatory peritoneal dialysate (CAPD), an intermittent peritoneal dialysate (IPD), a low Ca-CAPD dialysate or a dialysate for any other purpose, and may vary within the following ranges:

Electrolyte concentrations (mEq/l)

| | |
|---|---|
| $Na^+$ | 125–150 |
| $K^+$ | as needed |
| $Ca^{2+}$ | 0–6 |
| $Mg^{2+}$ | 0–3 |
| $Cl^-$ | 90–135 |
| Acetate$^-$ or lactate$^-$ | 0–40 |
| $HCO_3^-$ | 1–40 |
| Glucose (g/dl) | 1–5 |
| Osmotic pressure (mOsm/l) | 300–680 |
| pH | 5.7–7.5 |

The concentration of bicarbonate ions ($HCO_3-$) is desirably from 1 to 40, especially 4 to 40 mEq/l, with a range of from 20 to 30 mEq/l being more preferred. A bicarbonate ion concentration lower than the above range cannot sufficiently prevent electrolyte imbalance, whereas a bicarbonate ion concentration higher than the above range involves the potential problem that alkalosis may be induced. As the dialysate is stored in an amount of 2l in the container main body 112 in this embodiment, sodium bicarbonate is used in a range of from 0.168 g to 6.52 g. In view of the addition of the bicarbonate 56, it is desired to reduce the amount of the acetate or lactate in inverse proportion to the amount of the bicarbonate so added. For example, assuming that the concentration of bicarbonate ions ($HCO_3^-$) is 24 mEq/l, the concentration of lactate ions preferably ranges from 0 to 30 mEq/l. Further, the dialysate is desired to have a pH of from 5.7 to 7.5, especially from 6.2 to 7.2. Insofar as the pH of the dialysate falls in such a range, the dialysate is free from the potential problem that a stomach ache or the like may be caused upon dialysis.

The peritoneal dialysate is filled by dividing it into the bicarbonate 116 and the base solution 114. The bicarbonate 116 is filled in the connected container 115, and the interior of the connected container 115 is maintained in an alkaline state. Namely, the bicarbonate is filled in a solid alkali metal salt form in the connected container 115. The alkali metal in such an alkali metal salt substitutes for a portion of the corresponding alkali metal salt to be added to the base solution 114 which is in turn to be filled in the container main body 112. In this embodiment, it is desired to fill sodium bicarbonate or sodium carbonate in the connected container 115 in an amount sufficient to prepare a peritoneal dialysate of pH 7 or higher, especially of from pH 7.9 to pH 9.0 (this pH means a value when a 1:30 aqueous solution is prepared). The sodium salt to be added to the base solution 114 should be reduced by an amount equivalent to the sodium salt to be filled in the connected container 115.

As the base solution 114 is filled in the container main body 112 and the bicarbonate salt 116 is separately filled in the connected container 115, the base solution 114 is filled as a solution of a composition calculated by subtracting a lactate and a sodium salt in amounts as much as the theoretical amount of sodium in the bicarbonate 116.

Before being mixed with the bicarbonate 116, the pH of the base solution 114 is desirably 5.5 or lower, particularly 5.3 or lower, with 5.0 or lower being more desired. Such acidification of the base solution 114 can be easily achieved owing to the separation of the bicarbonate 116. When the base solution 114 is maintained at a pH in the above range, the potential problem that glucose or the like in the base solution 114 could undergo a quality modification is extremely reduced even when the base solution 114 is heated during autoclave sterilization.

The container main body 112 is provided with delivery ports 123. The base solution 114 is filled through one of the delivery ports 123. Both the delivery ports 123 are then closed in a liquid-tight fashion, followed by autoclave sterilization with the connected container 115 connected to the container main body 112. This autoclave sterilization is conducted based on the standards for steam sterilization as specified in the Pharmacopoeia of Japan. An ordinary autoclave is used for the autoclave sterilization. The autoclave sterilization is performed at a temperature of from 100° to 130° C. after purging the interior of the autoclave, for example, with an inert gas.

In the peritoneal dialysate container 111 constructed as described above, the bicarbonate 116 does not undergo decomposition during sterilization even under the severe heating conditions for the sterilization so that the bicarbonate 116 is stored in its filled state in the connected container 115. During storage of the container 111, the base solution 114 and the bicarbonate 116 are stored within the container main body 112 without decomposition. These peritoneal dialysate containers 111 can therefore be supplied, as are, not only to hospitals but also to patients'homes.

Peritoneal dialysate containers 111 of this embodiment were evaluated as will be described hereinafter. In each peritoneal dialysate container 111, 5.000 g of sodium bicarbonate powder were filled in the connected container 115. The base solution 114 was prepared with the above-described electrolytes and saccharide contained in the corresponding ranges also described above. Two liters of the base solution 114 were filled in the container main body 112. The seal portions 113 and 122 were formed in the above-described manner, followed by autoclave sterilization at 121° C.

The pealable seal portion 122 of each peritoneal dialysate container 111 was opened and the sodium bicarbonate was quantitated based on the Pharmacopoeia of Japan. As a result, changes in the amounts of sodium bicarbonate in all the peritoneal dialysate containers 111 before and after the autoclave sterilization were within ±5% by weight.

Upon use of the peritoneal dialysate container 111, the pealable seal portion 122 is pealed from the outside of the container main body 112 to communicate the interior of the container main body 112 and that of the connected container 115 with each other. The base solution 114 and the bicarbonate 116 are hence mixed, whereby the dialysate is prepared in the container main body 112.

Figure 13:
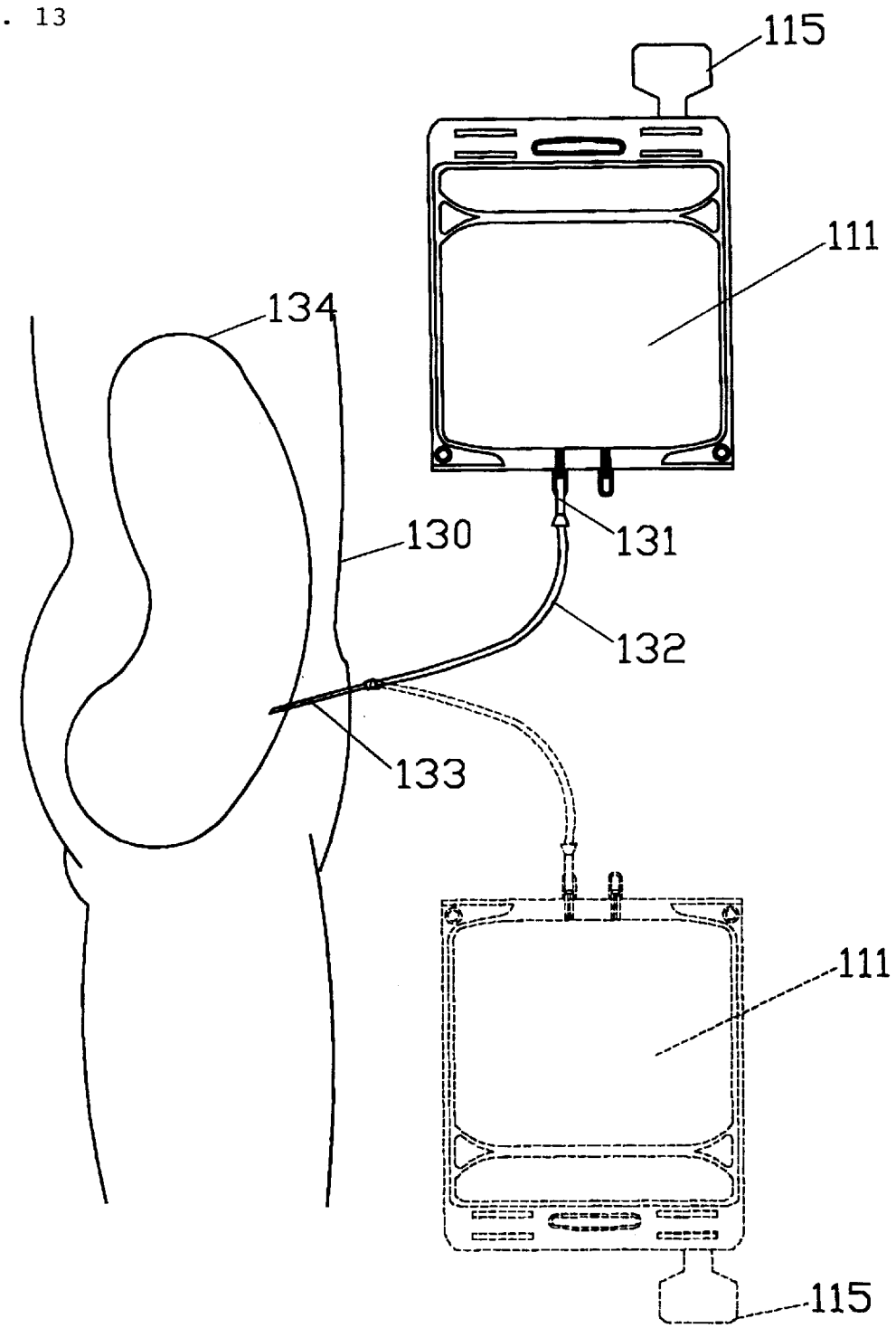
FIG. 13 is a schematic view illustrating the peritoneal dialysate container according to the fourth embodiment in use for a patient.

As is illustrated in FIG. 13, to apply the peritoneal dialysate to a patient 130 subsequent to the peeling of the pealable seal portion 122, a connecting tube 132 is brought into communication with the interior of the container main body 112 via a communication needle 131 pierced through one of the delivery ports 123 of the container 112. The connecting tube 132 is connected to a catheter 133, which is in turn connected to the interior of the abdominal cavity 134 of the patient 130. As a result, the dialysate in the container main body 112 is allowed to flow into the abdominal cavity 134 so that dialysis is performed.

We claim:

1. A sealed medical container containing an electrolyte solution comprised of a base solution and bicarbonate, each separately accommodated therein comprising:

a resin-made container body;

at least two compartments defined by an isolation wall, formed in said container body, said isolation wall being provided with an operable structure for aseptically communicating said at least two compartments when used;

said base solution accommodated in at least one but not all of said at least two compartments, said base solution having a pH of less than 5 and being sterilized after being accommodated in said at least one compartment;

said bicarbonate accommodated in the remaining compartment or compartments, said bicarbonate being an alkaline metal salt in a solid form and being sterilized after being accommodated in said remaining compartment(s);

wherein said operable structure is activated to aseptically communicate and mix said base solution and said bicarbonate when used; and said electrolyte solution having a pH in a range of from 3 to 10 and containing an $HCO_3$ at a concentration of from 1 to 65 mEq/l.

2. A sealed medical container according to claim 1, wherein said openable structure of said isolation wall is formed of a peelable seal portion.

3. A sealed medical container according to claim 2, wherein said peelable seal portion is made of a blend of polyethylene and polypropylene.

4. A sealed medical container according to claim 1, wherein the mixture of said base solution and said bicarbonate forms an infusion solution having a pH in the range of from 5.5 to 7.5 and containing an $HCO_3$ at a concentration of from 1 to 65 nEq/l.

5. A sealed medical container according to claim 1, wherein the mixture of said base solution and said bicarbonate forms a peritoneal dialysate containing:

an $HCO_3$ at a concentration of from 1 to 40 mEq/l, an $Na^+$ at a concentration of from 90 to 150 mEq/l, a $Ca^{2-}$ at a concentration of from 0 to 6 mEq/l, an $M6,+$ at a concentration of from 0 to 3 mEq/l, a Cl⁻ at a concentration of from 90 to 135 mEq/l a CH₃COO⁻ or CH₃CH(OH)COO⁻ at a concentration of from 0 to 40 mEq/l, and a saccharide or saccharides; and having:

an osmotic pressure in the range of from 300 to 680 mOsm/l, and a pH in the range of from 5.7 to 7.5.

6. A sealed medical container according to claim 1, wherein the mixture of said base solution and said bicarbonate forms an organpreserving solution containing:

an HCO₃⁻ at a concentration of from 1 to 50 mEq/l; and having:

an osmotic pressure in the range of from 250 to 400 mOsm/l, and a pH in the range of from 3 to 10.

7. A sealed medical container according to claim 1, wherein said electrolyte solution is an infusion solution, a peritoneal dialysate, or an organ-preserving solution, each having a pH of 6.0–8.0.

8. A sealed medical container according to claim 1, wherein said base solution is sterilized substantially with high-pressure steam after being accommodated in said at least one compartment, and wherein said bicarbonate is sterilized substantially with radiation after being accommodated in said remaining compartment(s).

9. A sealed medical container according to claim 8, wherein radiation sterilization is conducted using γ rays, electron beams, or ultraviolet rays.

10. A sealed medical container according to claim 4, wherein said radiation sterilization is electron beam sterilization at an accelerating voltage of 1 MeV or lower, and wherein each compartment accommodating said bicarbonate has a wall having a thickness of from 10 to 1,600 μm such that an electron beam penetrates said wall.

11. A sealed medical container according to claim 9, wherein said radiation sterilization is ultraviolet ray sterilization, and wherein each compartment accommodating said bicarbonate has a wall having a thickness of from 10 to 100 μm, and an ultraviolet transmission of at 60% or higher as measured at a wavelength of 250 μm when the thickness is 10 μm, and a density of from 0.95 to 0.85 g/cm³.

12. A method of producing a sealed medical container containing an electrolyte solution comprised of a base solution and bicarbonate, each separately accommodated therein, said bicarbonate being an alkaline metal salt in a solid form, comprising the steps of:

preparing a medical container comprising: a resin-made container body; and at least two compartments defined by an isolation wall, formed in said container body, said solution wall being provided with an openable structure for aseptically communicating said at least two compartments when used;

accommodating said base solution in at least one but not all of said at least two compartments and sealing the same;

sterilizing said accommodated base solution substantially with high-pressure steam;

accommodating said bicarbonate in the remaining compartment or compartments and sealing the same; and sterilizing said accommodated bicarbonate substantially with radiation, wherein the mixture of said base solution and said bicarbonate forms an electrolyte solution containing HCO₃.

13. A method of producing a sealed medical container according to claim 12, wherein the radiation sterilization is conducted using γ rays, electron beams, or ultraviolet rays.

14. A method of producing a sealed medical container according to claim 12, wherein said radiation sterilization is electron beam sterilization at an accelerating voltage of 1 MeV or lower, and wherein each compartment accommodating said bicarbonate has a wall having a thickness of from 10 to 1,600 μm such that an electron beam penetrates said wall.

15. A method of producing a sealed medical container according to claim 12, wherein said radiation sterilization is ultraviolet ray sterilization, and wherein each compartment accommodating said bicarbonate has a wall having a thickness of from 10 to 100 μm, and an ultraviolet transmission of at 60% or higher as measured at a wavelength of 250 nm when the thickness is 10 μm, and a density of from 0.95 to 0.85 g/cm³.

16. A method of producing a sealed medical container according to claim 12, wherein said electrolyte solution is an infusion solution, a peritoneal dialysate, or an organpreserving solution, each having a pH of 6.0–8.0, and wherein said base solution has a pH of 5.5 or lower to prevent deterioration of said base solution during high-pressure steam sterilization.

17. A method of producing a sealed medical container according to claim 16, wherein the base solution has a pH of less than 5.0.

* * * * *

UNITED STATES PATENT AND TRADEMARK OFFICE
CERTIFICATE OF CORRECTION

PATENT NO. : 5,871,477
DATED : February 16, 1999
INVENTOR(S) : Keinosuke Isono et al.

It is certified that error appears in the above-identified patent and that said Letters Patent is hereby corrected as shown below:

Column 22,
Line 58, delete "$HCO_3$" and insert -- $HCO_3^-$ --;
Line 60, delete "65 nEq/l" and insert -- 65 mEq/l --,
Line 63, delete "$HCO_3$" and insert -- $HCO_3^-$ --,
Line 67, delete "M6,+at" and insert -- $Mg^{2+}$ at --.

Signed and Sealed this

Twenty-first Day of October, 2003

JAMES E. ROGAN
*Director of the United States Patent and Trademark Office*